(12) United States Patent
Reilly

(10) Patent No.: US 9,480,791 B2
(45) Date of Patent: Nov. 1, 2016

(54) PUMPING DEVICES, SYSTEMS AND METHODS FOR USE WITH MEDICAL FLUIDS INCLUDING COMPENSATION FOR VARIATIONS IN PRESSURE OR FLOW RATE

(75) Inventor: David M. Reilly, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 1358 days.

(21) Appl. No.: 12/974,549

(22) Filed: Dec. 21, 2010

(65) Prior Publication Data
US 2011/0152681 A1 Jun. 23, 2011

Related U.S. Application Data

(60) Provisional application No. 61/288,732, filed on Dec. 21, 2009.

(51) Int. Cl.
*A61M 5/145* (2006.01)
*A61M 5/142* (2006.01)
*A61M 5/168* (2006.01)

(52) U.S. Cl.
CPC ......... *A61M 5/1452* (2013.01); *A61M 5/1422* (2013.01); *A61M 5/16881* (2013.01); *A61M 2005/14533* (2013.01); *A61M 2206/22* (2013.01)

(58) Field of Classification Search
CPC ........... A61M 5/1422; A61M 5/1452; A61M 2206/22; A61M 2005/14533
USPC .................................. 604/67, 151, 152, 153
See application file for complete search history.

(56) References Cited

U.S. PATENT DOCUMENTS

| | | | |
|---|---|---|---|
| 2,114,565 | A | 4/1938 | Kovach |
| 3,447,479 | A | 6/1969 | Rosenberg |
| 3,949,746 | A | 4/1976 | Wallach |
| 3,993,061 | A | 11/1976 | O'Leary |
| 3,994,294 | A | 11/1976 | Knute |
| 4,032,263 | A | 6/1977 | Pareja |
| 4,137,011 | A | 1/1979 | Rock |

(Continued)

FOREIGN PATENT DOCUMENTS

| | | |
|---|---|---|
| DE | 43363361 | 5/1994 |
| FR | 27153101 | 7/1995 |
| GB | 1511715 | 5/1978 |

OTHER PUBLICATIONS

International Search Report for International Application No. PCT/US 98/02027 filed Feb. 5, 1998.

(Continued)

*Primary Examiner* — Laura Bouchelle
*Assistant Examiner* — Anh Bui
(74) *Attorney, Agent, or Firm* — Joseph L. Kent; David Schramm; James R. Stevenson

(57) ABSTRACT

A system for delivery of a medical fluid to a patient includes a pump system including a pressurizing unit to pressurize the medical fluid and a drive system in operative connection with the pressurizing unit. The pump system exhibits variation in pressure during operation. The system further includes a compensating system in fluid connection with the medical fluid pressurized by the pressurizing unit. The compensating system defines a displacement volume in fluid connection with the pressurized medical fluid that is altered in a predetermined manner to alter the variation in pressure. The compensating system can, for example, reduce pulsatility of pressure during flow.

15 Claims, 18 Drawing Sheets

(56) References Cited

U.S. PATENT DOCUMENTS

| | | | |
|---|---|---|---|
| 4,236,880 A | * | 12/1980 | Archibald ......... A61M 5/14224 138/30 |
| 4,310,420 A | | 1/1982 | Konishi et al. |
| 4,311,586 A | | 1/1982 | Baldwin et al. |
| 4,475,666 A | | 10/1984 | Bilbrey et al. |
| 4,525,165 A | * | 6/1985 | Fischell ............ A61M 5/14276 128/DIG. 12 |
| 4,563,175 A | | 1/1986 | LaFond |
| 4,595,595 A | | 6/1986 | Gunnerson et al. |
| 4,734,011 A | * | 3/1988 | Hall, Jr. .............. F04B 11/0075 417/2 |
| 4,795,441 A | | 1/1989 | Bhatt |
| 4,838,860 A | | 6/1989 | Groshong et al. |
| 4,846,797 A | | 7/1989 | Howson et al. |
| 4,883,409 A | * | 11/1989 | Strohmeier et al. ............ 417/43 |
| 4,898,579 A | | 2/1990 | Groshong et al. |
| 5,044,902 A | | 9/1991 | Malbec |
| 5,066,282 A | | 11/1991 | Wijay et al. |
| 5,078,580 A | | 1/1992 | Miller et al. |
| 5,192,269 A | | 3/1993 | Poli et al. |
| 5,197,438 A | | 3/1993 | Kumano et al. |
| 5,237,309 A | | 8/1993 | Frantz et al. |
| 5,243,982 A | | 9/1993 | Mostl et al. |
| 5,378,231 A | | 1/1995 | Johnson et al. |
| 5,411,485 A | | 5/1995 | Tennican et al. |
| 5,417,667 A | | 5/1995 | Tennican et al. |
| 5,429,485 A | | 7/1995 | Dodge |
| 5,454,792 A | | 10/1995 | Tennican et al. |
| 5,496,273 A | | 3/1996 | Pastrone et al. |
| 5,529,463 A | | 6/1996 | Layer et al. |
| 5,609,572 A | | 3/1997 | Lang |
| 5,632,606 A | | 5/1997 | Jacobsen et al. |
| 5,852,231 A | | 12/1998 | Kaji |
| 5,916,197 A | | 6/1999 | Reilly |
| 6,197,000 B1 | | 3/2001 | Reilly |
| 8,133,205 B2 | | 3/2012 | Rhinehart et al. |
| 2008/0213115 A1 | * | 9/2008 | Hilger et al. ................. 417/569 |

OTHER PUBLICATIONS

Debiotech Switzerland, Sales Brochure, Lausanne 9, Switzerland, distributed week of Dec. 1, 1996 at the Radiological Society of North Americanin Chicago, Illinois.

* cited by examiner

Fig. 1B
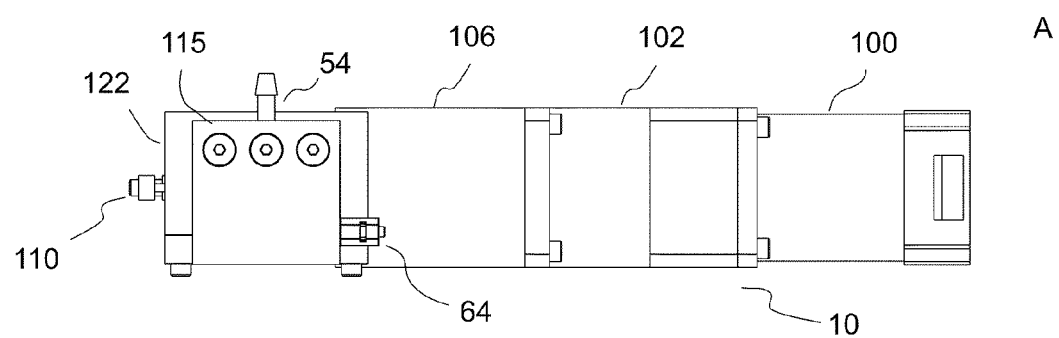
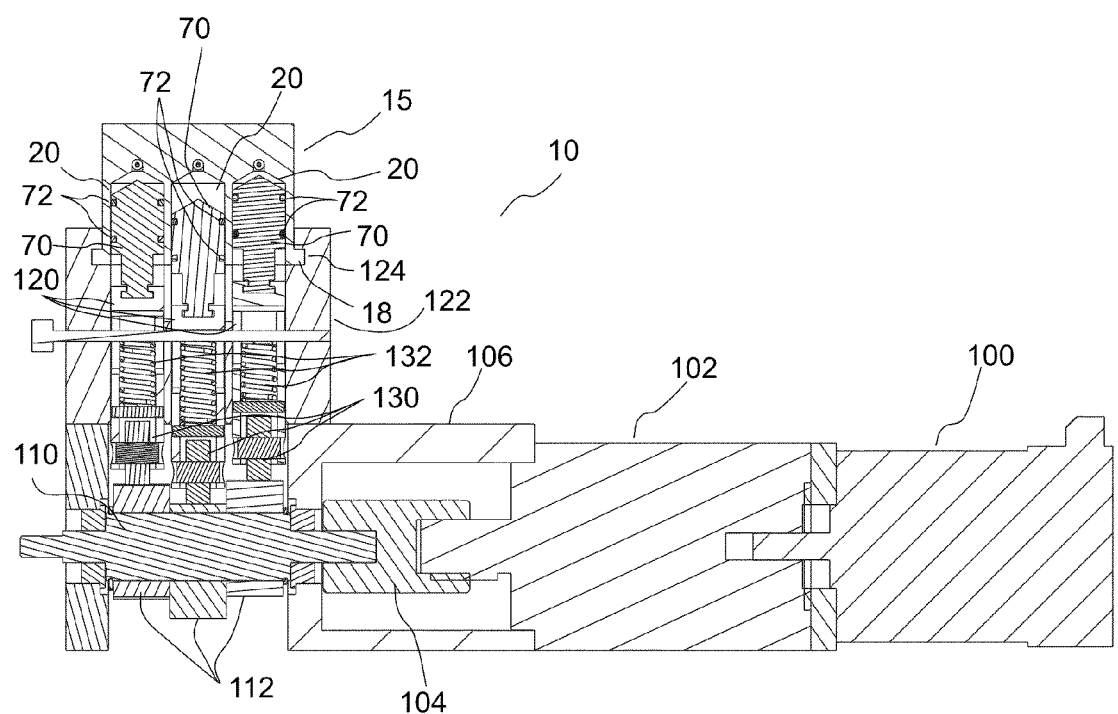
Fig. 1C

PUMPING DEVICES, SYSTEMS AND METHODS FOR USE WITH MEDICAL FLUIDS INCLUDING COMPENSATION FOR VARIATIONS IN PRESSURE OR FLOW RATE

CROSS-REFERENCE TO RELATED APPLICATION

This application claims the benefit of U.S. Provisional Application Ser. No. 61/288,732, filed on Dec. 21, 2009, the disclosure of which is incorporated herein by reference.

BACKGROUND OF THE INVENTION

The following information is provided to assist the reader to understand the devices, systems and/or methods described herein and the environment in which such devices, systems and/or methods will typically be used. The terms used herein are not intended to be limited to any particular narrow interpretation unless clearly stated otherwise in this document. References set forth herein may facilitate understanding of the devices, systems and/or methods or the background. The disclosure of all references cited herein are incorporated by reference.

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), CT scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

In the case of relatively high pressure applications, such as CT and angiography, mechanized syringe injectors are often used. In general, syringe pumps can deliver a fluid with good control of both pressure and flow rate. However, flow rate acceleration of syringe injectors is limited by the inertia of the extensive drive train required to translate motor rotation into syringe plunger motion. Moreover, syringe pumps are limited in that the maximum volume that can be injected at one time is the volume of the syringe.

Various pump systems for generally continuous delivery of fluids from large volume sources of fluid are available. However, it is often difficult to accurately control the pressure and flow rate of the fluid exiting the pumping system. In relatively low pressure applications, for example, peristaltic pumps have long been used. However, peristaltic pumps are difficult to control with accuracy.

Cost-effective and efficient pumping systems including a plurality of pressurizing members actuated in a timed manner to provide pressurization for injection of contrast and other liquid media are, for example, described in U.S. Pat. Nos. 6,197,000 and 5,916,197. Although, such pumps provide good control of pressure and flow rate, some variance in the pressure and/or flow rate can be experienced. Timed or sequential actuation of a plurality of pressurizing members or elements (for example, pistons, vanes, etc.) can, for example, result in pulsatile variations in pressure and/or flow rate. In general, pulsatile variations are repetitive variations or variations that occur with a certain frequency (for example, the frequency of activation of the pressurizing member(s)).

SUMMARY OF THE INVENTION

In one aspect, a system for delivery of a fluid (for example, delivery of a medical fluid to a patient) includes a pump system including a pressurizing unit to pressurize the medical fluid and a drive system in operative connection with the pressurizing unit. The pump system exhibits variation in pressure during operation. The system further includes a compensating system in fluid connection with the medical fluid pressurized by the pressurizing unit. The compensating system defines a displacement volume in fluid connection with the pressurized medical fluid that is altered (in a determined manner) to alter the variation in pressure. The compensating system can, for example, reduce pulsatility of pressure during flow.

The compensating system can, for example, include a moveable member in fluid connection with the pressurized medical fluid. The moveable member can be moveable to alter the displacement volume. The moveable member can, for example, be biased in a determined manner to oppose the force of the pressurized medical fluid upon the moveable member. In several embodiments, the moveable member is biased by a biasing mechanism or by a compressible fluid. The biasing mechanism can, for example, be a spring.

The moveable member can include a piston. The moveable member can include a flexible element that is biased by a compressible fluid.

In several embodiments, the compensating system includes a rigid conduit, and the flexible element includes a flexible conduit within a lumen of the rigid conduit. A compressible fluid is entrapped between the rigid conduit and the flexible conduit. The lumen of the flexible conduit is in fluid connection with the pressurized medical fluid. The lumen of the flexible conduit can, for example, be in fluid connection with an outlet of the pump system.

In a number of embodiments, the pressurizing unit includes a plurality of pressurizing members actuated in a timed manner by the drive system. The movable members can be moved in a timed manner dependent upon timing of actuation of the pressurizing members. The movable member can, for example, be in operative connection with a drive mechanism adapted to move the moveable member in a timed manner dependent upon timing of actuation of the pressurizing members. The drive mechanism can, for example, include a multi-lobed cam element that is rotated to impart timed movement of the moveable member. The number of lobes of the multi-lobed cam element can be determined by a number of the pressurizing members. For example, the number of lobes can equal the number of pressurizing members or be some multiple, divisor or quotient thereof. The pump system can, for example, include a rotatable timing shaft, such as a cam shaft or a crank shaft, to actuate the pressurizing members in the timed manner, and the multi-lobed cam element can be coupled to the timing shaft.

The moveable member can, for example, include a piston slidably positioned within a chamber and forming a sealing engagement with an inner wall of the chamber. The extent to which the piston can alter the displacement volume can be adjustable. For example, a rearwardmost position of the piston can be adjustable within the chamber to adjust an extent to which the piston can alter the displacement volume. The piston can, for example, be biased against the force of the pressurized medical fluid by a biasing mechanism. The biasing mechanism can be a spring. The system can further include an abutment element to abut the piston and to adjust the rearwardmost position of the piston.

In a number of embodiments, the moveable member includes a piston slidably positioned within a chamber and forming a sealing engagement with an inner wall of the chamber and an actuator system to control the position of the piston within the chamber. The actuator system is in communicative connection with a control system, which can, for example, operate the actuator to control the position of the piston on the basis of at least one measured variable, such as pressure and/or flow rate (or a variable related to, proportional thereto or dependent thereon).

The compensating system can, for example, be in fluid connection with an outlet channel within the pressurizing unit. The pressurizing unit can be removable from connection with the drive system.

In another aspect, a compensating system for reducing variations in pressure of a fluid includes a rigid conduit and a flexible conduit within a lumen of the rigid conduit. A compressible fluid is entrapped between the rigid conduit and the flexible conduit. The flexible conduit includes an inlet to place the flexible conduit in fluid connection with the fluid. The flexible conduit can further include an outlet, and the flexible conduit can be adapted to be placed in-line with a flow of the fluid.

In another aspect, a compensating system for use in connection with pump system, which includes a pressurizing unit and a drive system, wherein the pressurizing unit includes a plurality of pressurizing members actuated in a timed manner by the drive system to pressurize a fluid, includes a movable member in operative connection with a drive mechanism adapted to move the moveable member in a manner dependent upon timing of actuation of the pressurizing members to alter a displacement volume in fluid connection with the pressurized fluid to reduce pulsatility in fluid pressure.

The drive mechanism can, for example, include a multi-lobed cam element that is rotated to time movement of the moveable member. The number of lobes of the multi-lobed cam element can be determined by a number of the pressurizing members.

The moveable member can include a piston slidably positioned within a chamber and forming a sealing engagement with an inner wall of the chamber.

A rearwardmost position of the piston can be adjustable within the chamber to adjust an extent to which the piston can alter the displacement volume. The piston can be biased against the force of the pressurized medical fluid by a biasing mechanism. The biasing mechanism can be a spring. The compensating system can further include an abutment element to abut the piston and to adjust the rearwardmost position of the piston.

The moveable member can include a piston slidably positioned within a chamber and forming a sealing engagement with an inner wall of the chamber. The compensating system can further include an actuator system to control the position of the piston within the chamber. The actuator system can in be operative connection with a control system which controls the actuator system based on measurement of at least one variable related to pressure or flow rate.

In a further aspect, a pressurizing unit for use with a pump system, which includes a drive system to power the pressurizing unit, includes a plurality of pressurizing members in connection with a fluid outlet channel and a first compensating system to reduce pulsatility in pressure in fluid connection with the outlet channel. The pressurizing unit can be removably connectible to the drive system.

The first compensating system can include a moveable member. The moveable member can be moveable to alter a displacement volume in fluid connection with the outlet channel. The moveable member can, for example, be biased by a biasing mechanism or by a compressible fluid.

The pressurizing members can be actuated in a timed manner by the drive system, and the first compensating system can further include a drive member adapted to move the moveable member in a manner dependent upon timing of actuation of the pressurizing members to alter the displacement volume. The drive member can be removably connectible to the drive system.

The pressurizing unit can, for example, be adapted to pressurize a fluid to achieve a flow rate of between 0 and 100 ml/sec (or any range therebetween). The pressurizing unit can, for example, be adapted to pressurize a fluid to achieve a pressure of between 10 and 2000 psi (and more typically between 25 and 1500 psi) or any range therebetween.

In another aspect, a compensating system to reduce pulsatility in pressure or flow in a pump system for pressurizing a fluid includes a moveable element defining a displacement volume in fluid connection with a conduit for the pressurized fluid, and a drive to move the moveable element in a timed manner. A maximum displacement volume associated with the moveable element can be adjustable as a function of pressure (or flow rate).

In a further aspect, a method of injecting a fluid into a patient, includes: providing a pump system including a pressurizing unit to pressurize the medical fluid and a drive system in operative connection with the pressurizing unit, the pump system exhibiting variation in pressure during operation; and providing a compensating system in fluid connection with the medical fluid pressurized by the pressurizing unit, the compensating system defining a displacement volume in fluid connection with the pressurized medical fluid that is altered (for example, in a determined manner) to alter the variation in pressure.

The devices, systems and/or methods described herein, along with the attributes and attendant advantages thereof, will best be appreciated and understood in view of the following detailed description taken in conjunction with the accompanying drawings.

BRIEF DESCRIPTION OF THE DRAWINGS

FIG. 1B illustrates a top view of the pump system of FIG. 1A.

FIG. 1C illustrates a side, cross-sectional view of the pump system of FIG. 1A.

DETAILED DESCRIPTION OF THE PRESENT INVENTION

Figure 1A:
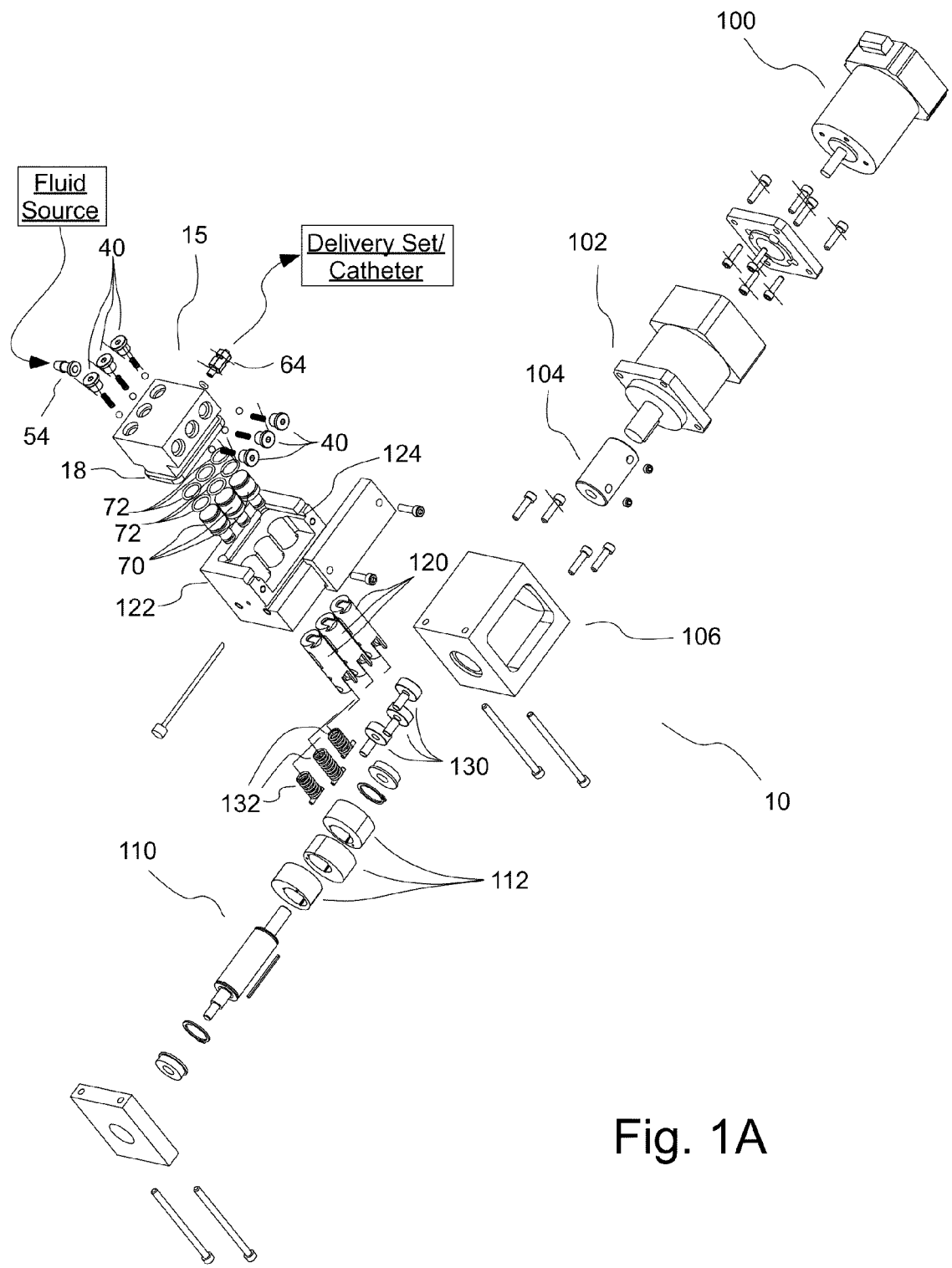
FIG. 1A illustrates a perspective, exploded or disassembled view of an embodiment of a pump system.
Figure 1D:
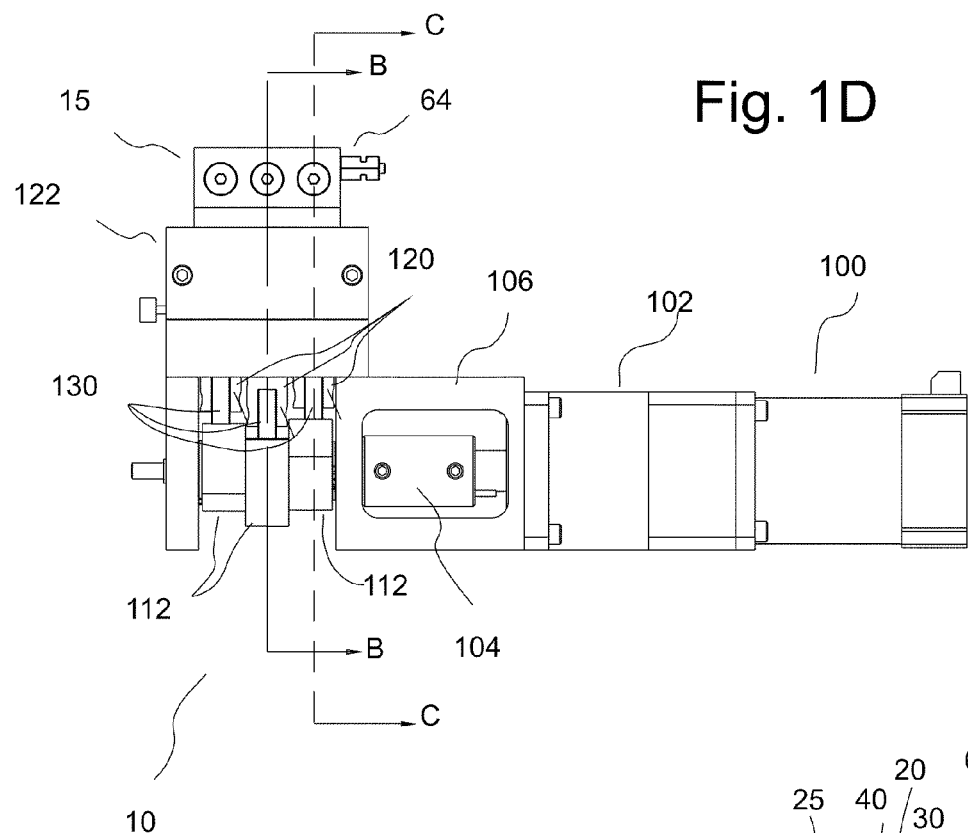
FIG. 1D illustrates a side view of the pump system of FIG. 1A.
Figure 1F:
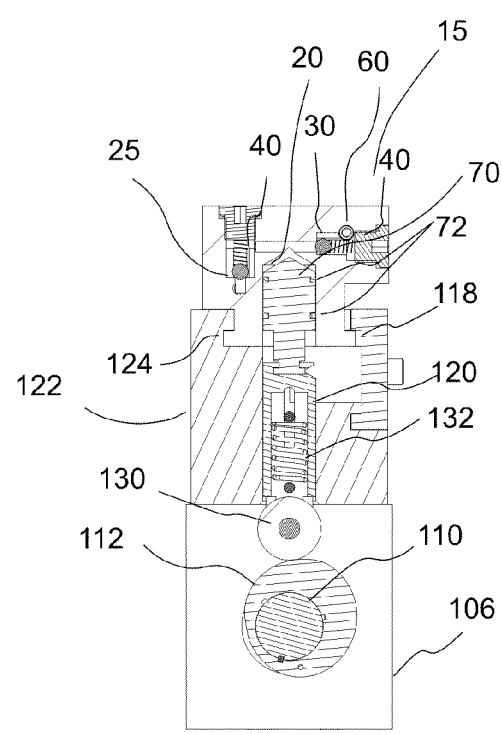
FIG. 1F illustrates a cross-sectional view of the pump system of FIG. 1A as defined by section C-C of FIG. 1D.
Figure 1E:
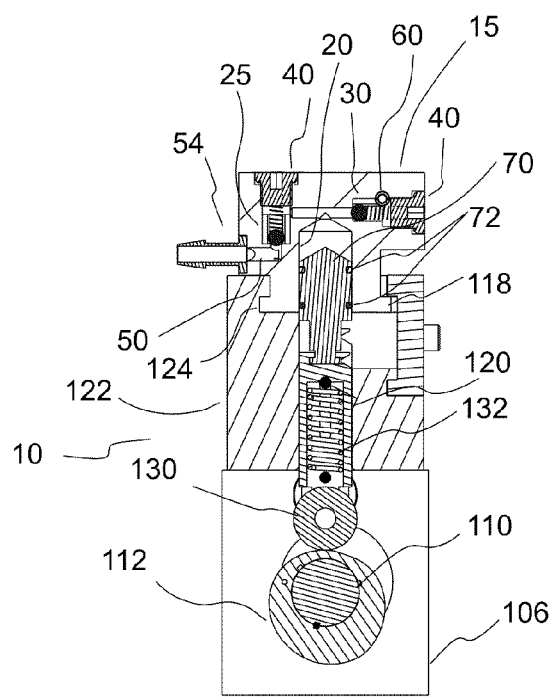
FIG. 1E illustrates a cross-sectional view of the pump system of FIG. 1A as defined by section B-B of FIG. 1D.

As used herein and in the appended claims, the singular forms "a," "an", and "the" include plural references unless the content clearly dictates otherwise. Thus, for example, reference to "a fluid displacement member" includes a plurality of such fluid displacement members and equivalents thereof known to those skilled in the art, and so forth, and reference to "the fluid displacement member" is a reference to one or more such fluid displacement members and equivalents thereof known to those skilled in the art, and so forth.

Devices, systems and methods described herein can, for example, be used to decrease variation (including, for example, pulsatile variation) in the pressure and/or flow rate of pump systems used in the delivery of, for example, medical fluids. The devices, systems and method can, for example, be used in connection with pumps including a plurality of pressurizing members or elements such as the multi-piston pumps of U.S. Pat. Nos. 6,197,000 and 5,916,197, gear pumps, gear rotors, vane pumps, peristaltic pumps and other pumps. In general, pump systems hereof used to pressurize medical fluids for injection into a patient operate over a pressure range of approximately 10 to 2000 psi (and more typically over a pressure range of approximately 25 to 1500 psi) and over a flow rate range of approximately 0 to 100 ml/sec (and more typically 0 to 50 ml/sec).

FIGS. 1A through 1F illustrate one embodiment of multi-cylinder pump system 10 which exhibits a certain degree or amount of pulsatile variation in pressure and/or flow rate. In the illustrated embodiment, three chambers 20 (see, for example, FIG. 1C) of a pressurizing unit 15 are in generally linear, side-by-side alignment (that is, the axes of chambers 20 are generally in the same plane). Each chamber 20 has an inlet port 25 and an outlet port 30 in fluid connection therewith.

Inlet ports 25 and outlet ports 30 can, for example, be provided with check valves or plug valves 40 to assist in maintaining the desired direction of flow. Inlet ports 25 are, for example, in fluid connection with a common inlet passage, conduit or channel 50, while outlet ports 30 are, for example, in fluid connection with a common outlet passage, conduit or channel 60. Inlet channel 50 is in fluid connection with an inlet port 54 (which, can for example, be in fluid connection with a barbed connector) for attachment to a source of fluid such as a contrast medium or other pharmaceutical/medical fluid, while outlet channel 60 is in fluid connection with an outlet port 64 (which can, for example, be in fluid connection with a connector such as a Luer connection) for connection, for example, to a delivery set, which can, for example, include a catheter, to deliver fluid to a patient.

Disposed within each chamber 20 is a pressurizing member or piston 70 suitable to alternatively draw the liquid medium into chamber 20 upon a downward or rearward stroke thereof and to expel/pressurize the liquid medium, forcing the pressurized liquid medium into outlet channel 60, upon an upward or forward stroke thereof. Motive force is provided to pistons 70 by, for example, an external motor-driven (or otherwise powered) drive mechanism or drive system 100 that imparts reciprocating linear motion to pistons 70. High pressures (for example, used in contrast medium injection in CT and angiographic procedures) in outlet channel 60 are possible with the proper choice of materials and wall thickness. One or more sealing members such as an O-ring 72 can be positioned between each piston 70 and the inner wall of chamber 20 to form a sealing engagement therewith.

Drive mechanism 100 can, for example, be in operative connection with a timing mechanism, system or shaft such as a cam shaft 110 to drive pistons 70 in a timed sequence, which can be chosen to minimize pulsatile flow. In the illustrated embodiment, drive mechanism 100 is in operative connection with cam shaft 110 via a gearbox 102, a coupling 104 and an adapter 106. Cam lobes 112 of cam shaft 110 can, for example, be in operative connection with cam lifters or piston extension members 120 which are reciprocally moveable through a lifter block 122 and terminate on one end thereof in attachment members which cooperate with corresponding attachment members on pistons 70. For example, slots on piston extension members can cooperate with flanges on pistons 70 to form a readily releasable connection between pistons 70 and piston extension members 120. Piston extension members 120 can, for example, be placed in operative connection with cam shaft lobes 112 via cam lifters 130 (which can, for example, including a bearing member which is attached to extension member 120 via a pin) in operative connection with lifter springs 132.

In a number of representative embodiments of pump system 10 (and other pump systems) used in the studies hereof, the bore diameter of each chamber 20 was approximately 0.625 inches and the stroke length of pistons 70 was approximately 0.364 inches, resulting in a displacement of 5.5 ml per revolution of cam shaft 110 for pump system 10. The chambers and pistons of the pump systems hereof can, for example, be dimensioned and operated to provide a range of fluid displacements per revolution. In a number of embodiments, pump systems hereof exhibit a displacement per revolution in the range of approximately 1 to 10 ml.

Pressurizing unit 15 can, for example, be placed in operative connection with lifter block 122 via a flange 18 which can be seated in a seating 124. In this manner, the fluid contacting portions of system 10, including pressurizing unit 15 can be readily removed from connection with drive mechanism 100. Pressurizing unit 15 can be disposable (for example, on a per-patient, per time or other basis) to, for example, reduce or eliminate the risk of cross-patient contamination. Pressurizing unit 15 can, for example, be formed relatively inexpensively from polymeric, metallic, ceramic and/or other materials by any number of processes including, molding, injection molding, co-injection molding, extrusion, machining etc.

In general, three-cylinder pump system 10 was designed to deliver continuous flow with minimal pulsatility. In that regard, cam shaft 110/cam lobes 112 were optimized to provide the best results, and other components were selected to provide the best output. However pulsatility remains in the flow. Theoretically, the fluid output associated with three cams shaft lobes 112 should be constant for a constant rotational velocity of cam shaft 110. As the pressure rises, however, and without limitation to any mechanism, it is believed that mechanical capacitance (for example, compression and stretch of components under load) causes delays in the rise of pressure associated with individual pistons 70. As the delay increases, the system fluid pressure drops in the region of overlap of output of the cylinders.

Pulsatility can be measured in terms of variations in flow rate or variations in pressure. As set forth in U.S. Pat. Nos. 6,197,000 and 5,916,197, a degree or percent of pulsatile flow can be defined with the following equation:

100%*(max flow−min flow)/average flow

The standard deviation from an average pressure and/or flow rate can provide another or alternative measure of pulsatility. In general, pressure is more easily measured than flow rate.

In general, flow rate in the system is directly related to pressure change. In a simple system of flow of an incompressible fluid in a pipe, this direct relationship can be shown from the following equation, derived from the Bernoulli equation:

$$p_B = p_A - \rho g\left(\Delta z + f\frac{L}{D}\frac{V^2}{2g}\right)$$

wherein, $p_B$ is pressure at point B, $p_A$ is pressure at point A, $\rho$ is fluid viscosity, g is the gravity acceleration constant, z is pipe elevation above some datum, f is a friction factor, D is pipe diameter, L is pipe length between point A and point B and V is the average velocity of the fluid. Likewise, for viscous, incompressible flow in a long pipe (that is, having a length significantly longer than its diameter) of circular cross-section, the Hagen-Pouiseulle equation provides $$Q = \int_0^R 2\pi v_z dr = \frac{\pi R^4}{8\mu}\frac{\Delta p}{L}$$

wherein Q is volumetric flow rate, R is the radius of the pipe, $\mu$ is dynamic fluid viscosity, L is the length of the pipe and $\Delta p$ is the pressure change. Although there is no corresponding simple equation to provide flow rate as a function of pressure in a pump system, the above equations are indicative of the direct relationship between flow rate and pressure (for example, as measured in outlet conduit 60 or at outlet 64) in a pump system.

Figure 1G:
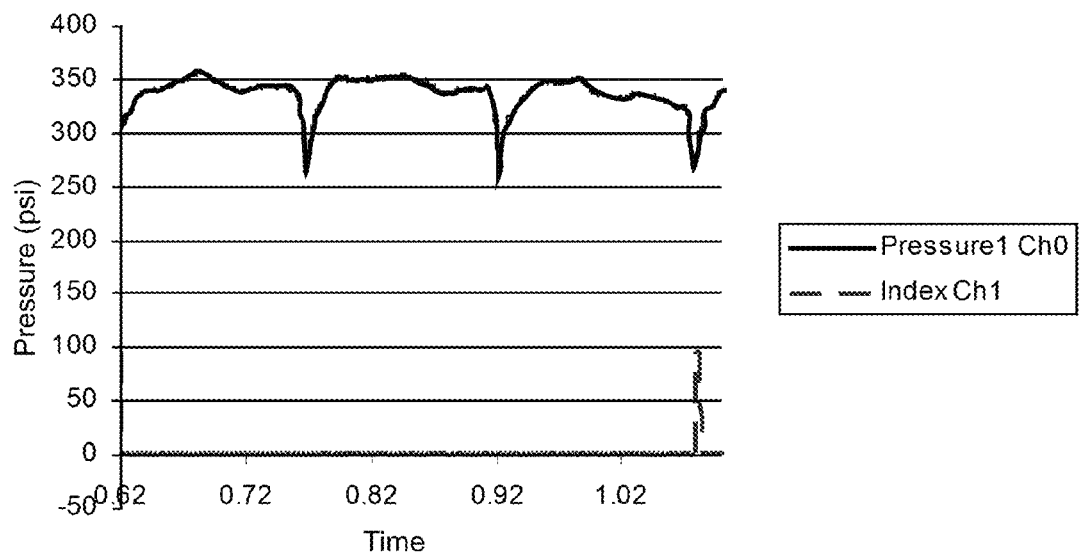
FIG. 1G illustrates a pulsatile variation in pressure over time observed with the pump system of FIG. 1A when operated at an average pressure of 300 psi for one revolution of the cam shaft of the pump system of FIG. 1A.
Figure 1H:
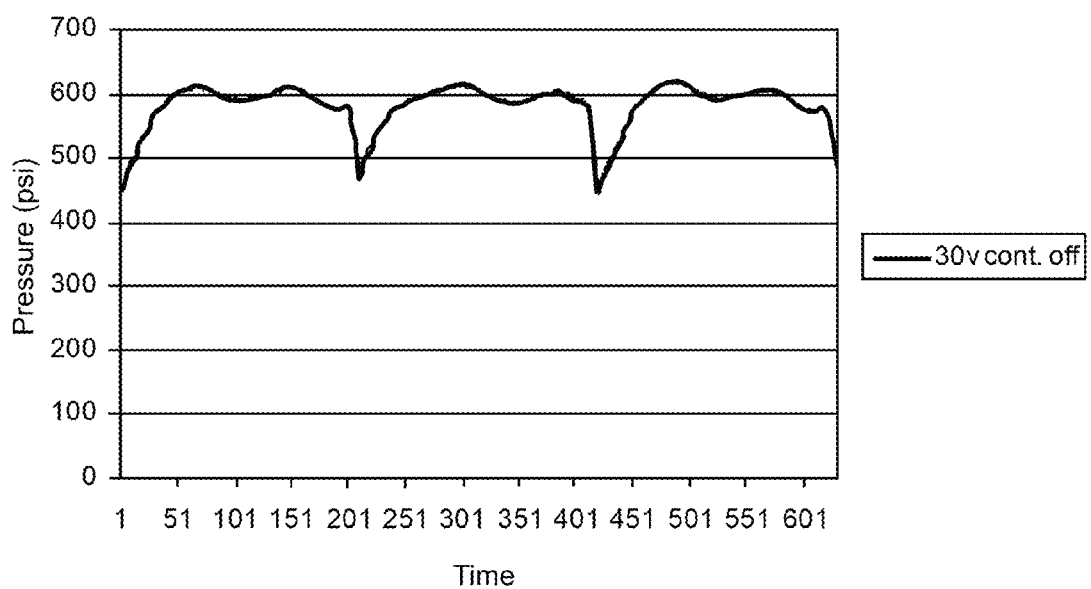
FIG. 1H illustrates a pulsatile variation in pressure over time observed with the pump system of FIG. 1A when operated at an average pressure of 600 psi for one revolution of the cam shaft of the pump system of FIG. 1A.

FIG. 1G illustrates a graph of pressure as a function of time for flow from pump system 10 for one revolution of cam shaft 110 at an average pressure of 300 psi. FIG. 1H illustrates a similar study at higher pressure of 600 psi. In the study illustrated in FIG. 1G, the average pressure was 337 psi. The maximum pressure was 357 psi, while the minimum pressure was 260 psi. As set forth above, the standard deviation from the average pressure can, for example, provide a measure of pulsatility.

In a number of embodiments, compensating systems or compensators are used in connection with a pump system (such as pump system 10) which exhibits some degree of pulsatility as determined, for example, by studying the pressure/flow rate profile (versus time) over a range of operating pressures/flow rates. As described herein, compensating systems can, for example, be designed on the basis of a determined profile to reduce pulsatility.

As such compensating systems come in contact with the fluid to be injected, the compensating system (or the fluid-contacting components thereof) can be made to be removable to, for example, be disposable (on a per-patient, per-time or other basis), thereby reducing or eliminating the risk of cross-patient contamination. The compensating system can, for example, be disposable with (or as a part of) pumping or pressurizing unit 15. The compensating system can, for example, be formed relatively inexpensively from polymeric, metallic, ceramic and/or other materials by any number of processes including, molding, injection molding, co-injection molding, extrusion, machining etc.

Figure 2A:
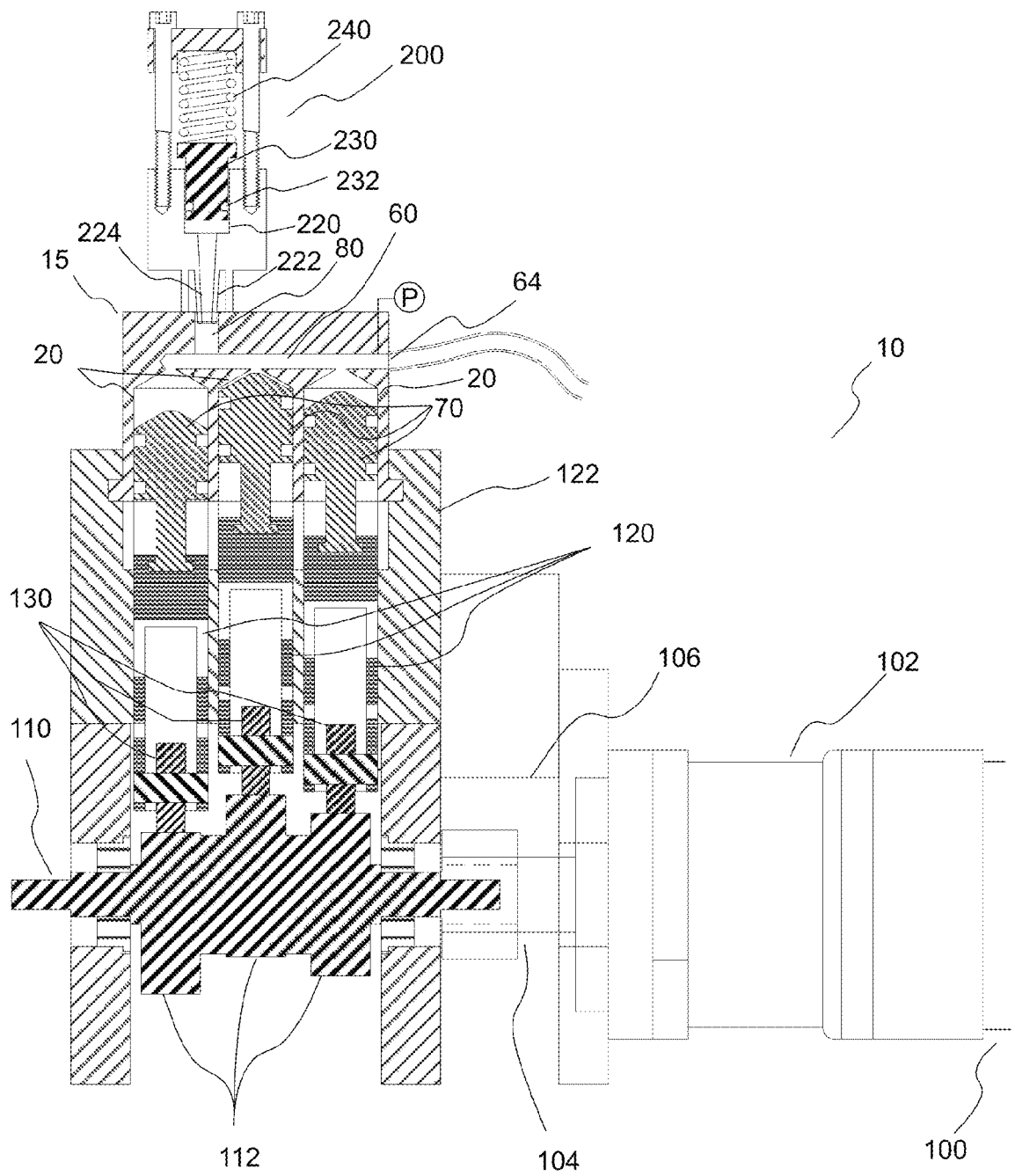
FIG. 2A illustrates a side, cross-sectional view of an embodiment of a compensating system or compensator in operative connection with the pressurizing unit of the pump system of FIG. 1A.
Figure 2C:
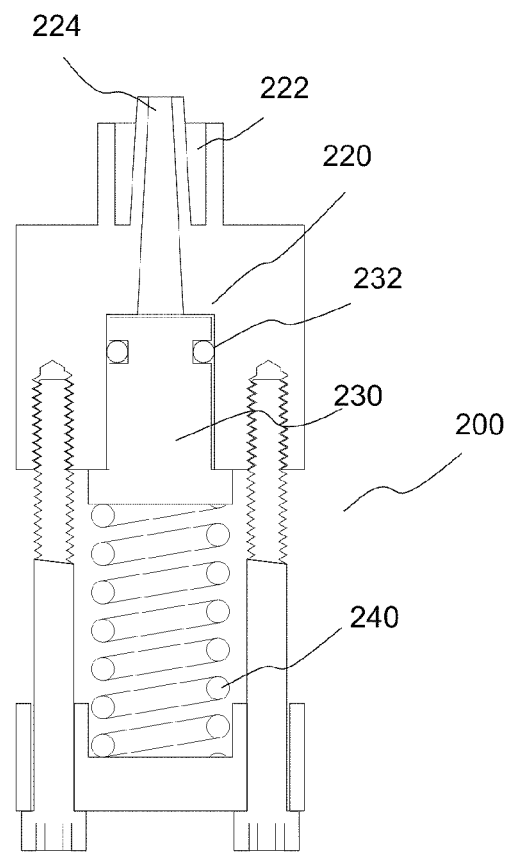
FIG. 2C illustrates a side, cutaway view of the compensating system of FIG. 2A wherein the fluid displacement member or piston thereof is in a forward position.
Figure 2B:
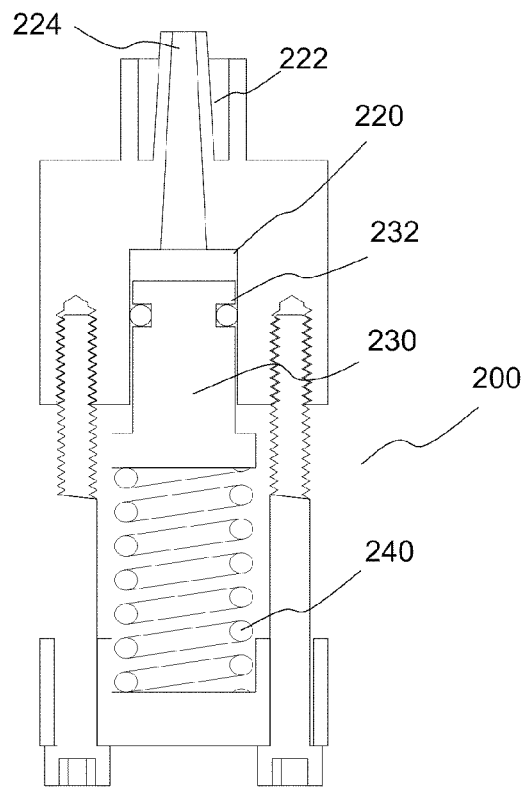
FIG. 2B illustrates a side, cutaway view of the compensating system of FIG. 2A wherein the fluid displacement member or piston thereof is in a rearward position.

FIGS. 2A through 2C illustrate one embodiment of a compensating system 200. In the illustrated embodiment, compensating system 200 includes a chamber 220 that is in fluid connection with pressurized fluid through, for example, outlet channel 60 via a port 80 formed in pressurizing unit 15. An outlet 222 of compensating system 200 can, for example, be formed with or connected to a Luer connector to connect to a cooperating connector of port 80. An outlet conduit 224 passing through outlet 222 places chamber 220 in fluid connection with port 80. In the illustrated embodiment, a fluid displacement member or piston 230 is slidably positioned within chamber 220. One or more sealing elements such as O-ring 232 can be used to create a sealing engagement with an inner wall of chamber 220. A biasing mechanism 240 such as a spring biases piston 230 against the force exerted thereon by the pressurized fluid.

To reduce pulsatility and achieve a more constant flow, compensating system 200 operates to change the volume of the output conduit/manifold 60 of the pump by displacing a certain volume of fluid in a manner to reduce short term, transient or pulsatile changes in flow rate and pressure. In general, compensating system 200 acts as a capacitor, accumulating volume when pressure is high, and delivering volume when pressure drops. Biased piston 230 is positioned by spring 240 to define an adjustable displacement volume (that is, the volume of chamber 220 forward of piston 230). In that regard, increased pressure in the system compresses spring 240 and increases the volume of output channel 60, thereby reducing flow (see, for example, FIG. 2B). As pressure drops, spring 240 pushes fluid out of chamber 220 and into outlet conduit or channel 60 (thereby increasing flow) to prevent flow from dropping (see FIG. 2C).

Using the data from FIG. 1G and the specific volume of pump system 10 (that is, volume (ml) delivered per revolution of cam shaft 110), the volume below the average associated with each area of pressure/flow rate drop can be calculated. In this example the volume below average is 0.216 ml per revolution. There are three main areas of drop in pressure/flow rate per revolution. These areas of flow rate drop average 0.216 ml/3 or 0.072 ml each.

In one representative example of a compensating system 200, the area of piston 230 was 0.110 in$^2$. As described above in connection with FIG. 1G, the average pressure for the system without the compensating system was 337 psi and the minimum pressure was 260 psi. The pressure change between the average pressure and the minimum pressure was 77 psi. The stroke of piston 220 required to compensate for the flow rate drop associated with each of the three drops per cycle is calculated by dividing that volume (0.072 ml) by the area of piston 220.

$$(0.072 \text{ ml}/16.39 \text{ ml/in}^3)/0.110 \text{ in. sq.} = 0.0399 \text{ in. travel.}$$

A desired spring constant for spring 240 can be calculated by multiplying the pressure differential by the piston area, which will equal the spring constant multiplied by the length of travel.

$$77 \text{ psi} \times 0.11 \text{ in sq} = K \times 0.0399 \text{ in.}$$

In the above equation, K=212 lb/in. A spring having a spring constant close to this value was chosen for studies of compensating system 200. A number of studies of pump system 10 including such a compensating system 200 are set forth in FIGS. 2D through 2G.

Figure 2D:
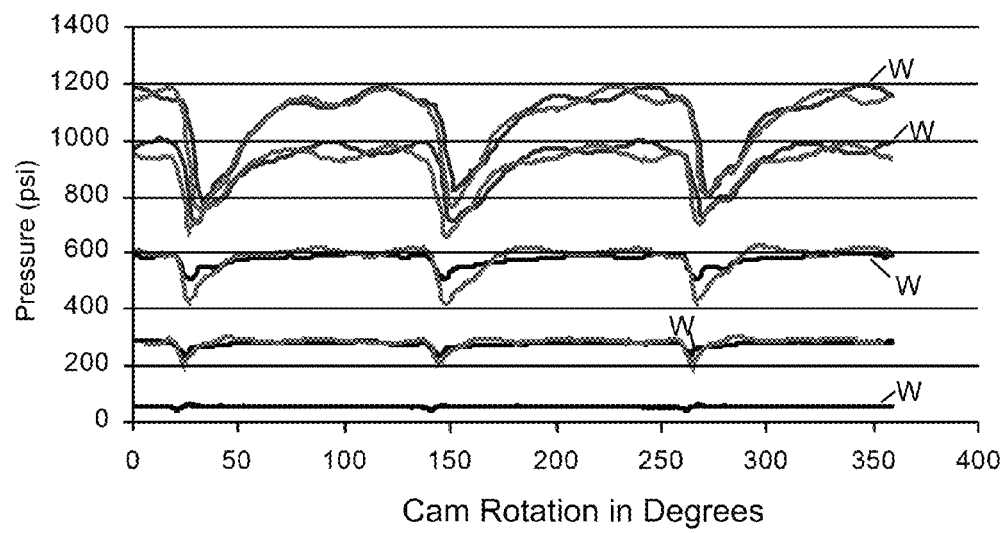
FIG. 2D illustrates a comparison of pressure as a function of cam shaft rotation for pump system 10 operated with and without the compensating system of FIG. 2A, wherein pressure curves created with the compensating system of FIG. 2A are labeled with the designation "W".

FIG. 2D shows the pressure wave form for one revolution of the pump at various pressures. The data show the effect of the addition of the compensating system at different pressures.

Figure 2E:
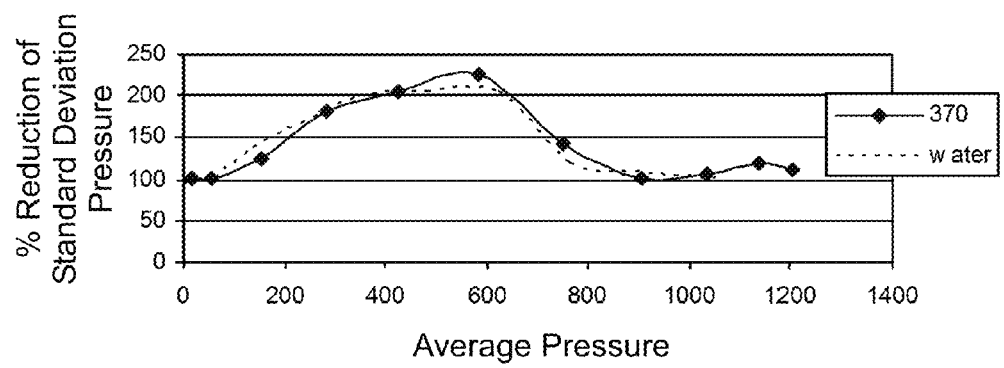
FIG. 2E illustrates the percent reduction in the standard deviation in pressure over a range of average operating pressure for the system of FIG. 2A for two different fluids.

FIG. 2E also shows the effect across the range of pressures for two fluids (water and ULTRAVIST® 370, a non-ionic contrast medium available from Bayer AG of Berlin, Germany). In the graph of FIG. 2E, a data point of 100% corresponds to no change, while a data point of 200% (as measured by the standard deviation of the pressure) represents a reduction in the standard deviation by one-half. As illustrated in FIG. 2E, the most effective range of compensating system 200 was between approximately 350 and 620 psi. In that regard, compensating system 200 was "tuned" or designed for operation in this general pressure range. As the curves are not linear, a single compensating system 200 is not equally effective across the full range of operation pressure.

Figure 2F:
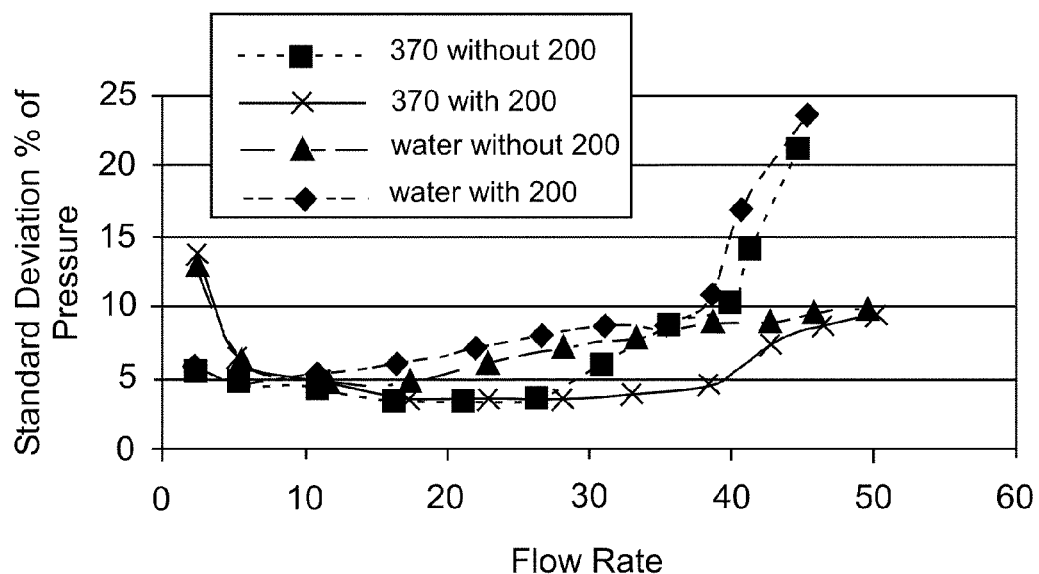
FIG. 2F illustrates standard deviation of pressure over a range of flow rates for pump system 10 operated with and without the compensating system of FIG. 2A for two different fluids.
Figure 2G:
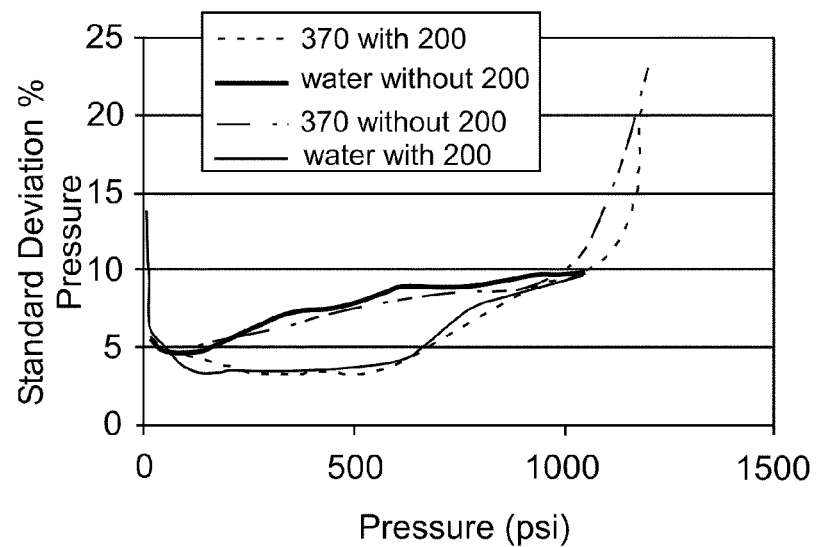
FIG. 2G illustrates standard deviation of pressure over a range of average operating pressure for pump system 10 operated with and without the compensating system of FIG. 2A for two different fluids.

In FIGS. 2F and 2G, pulsatility of pump system 10 is represented by standard deviation as a percent of the pressure (for example, as measured by a pressure sensor P as illustrated in FIG. 2A) as a function of flow rate and of pressure, respectively, for two fluids (water and ULTRAVIST 370). The data illustrate that the addition of compensating system 200 decreases the standard deviation of pressure of pump system 10.

Figure 3A:
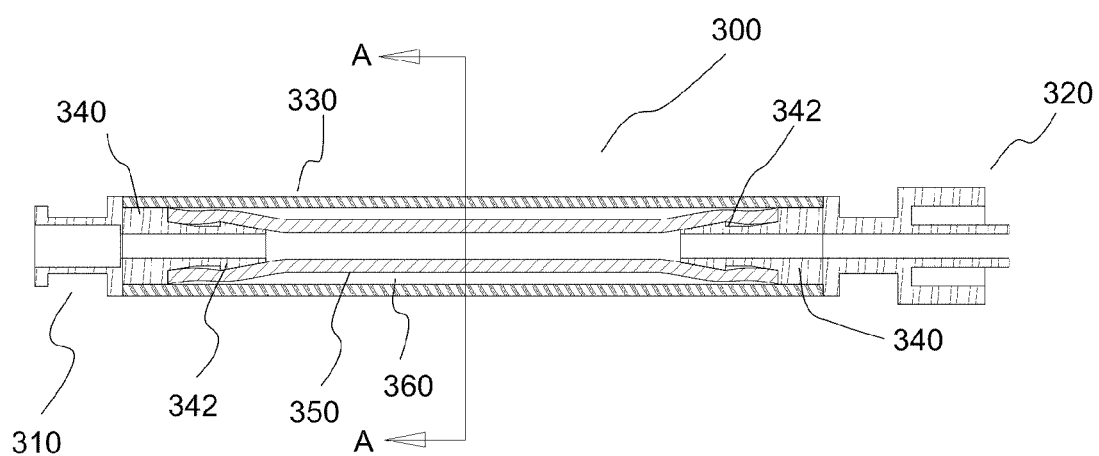
FIG. 3A illustrates a side, cross-sectional view of another embodiment of a compensating system or compensator.
Figure 3B:
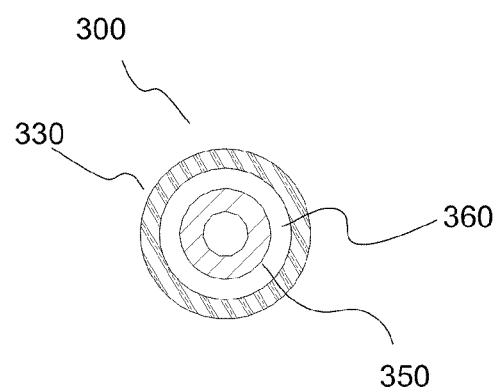
FIG. 3B illustrates a cross-sectional view of the compensating system of FIG. 3A along section A-A thereof.

FIGS. 3A and 3B illustrate another embodiment of a compensating system or compensator 300 for use in connection with a pump system, such as pump system 210. Compensating system 300 is designed to be placed in-line with pressurized fluid. For example, compensating system 300 can include a first connector 310 (for example, a female Luer connector) for connection to outlet port 64 of pump unit 15 and a second connector 320 (for example, a male Luer connector) for connection to a fluid delivery set. Compensating system 300 further includes an outer, rigid tube 330 that is attached to hubs 340 on each end. Rigid tube 330 prevents stretching of the assembly and assists in clamping a volume displacement member including a flexible tube or conduit 350 to, for example, hose barbs 342 on hubs 340. A volume 360 between the outer rigid tube 330 and inner flexible tube 350 creates a trapped volume containing a compressible fluid (for example, a gas such as air at ambient or another pressure) and operates similarly to biasing spring 240 of compensating system 200. In that regard, pressurized fluid from fluid pressurizing unit 15 flows through the lumen of interior tube 350. Expansion of flexible, inner tube 350 under pressures corresponds to expansion of piston 230 of compensating system 200. The strength/modulus of the material of flexible, internal tubing 350, its wall thickness and bore, as well as the pressure increase of the gas surrounding internal tube 350 in volume 360, provide a restorative or biasing force corresponding to that provided by spring 240 (or other biasing mechanism) of compensating system 200. In that regard, increased pressure in the system expands internal tube 350 and increases the volume thereof, thereby reducing flow. As pressure drops, the restorative forces described above cause compression of internal tube 350, reducing the volume, thereby increasing flow and reducing a drop in flow rate associated with the pressure drop.

Figure 4A:
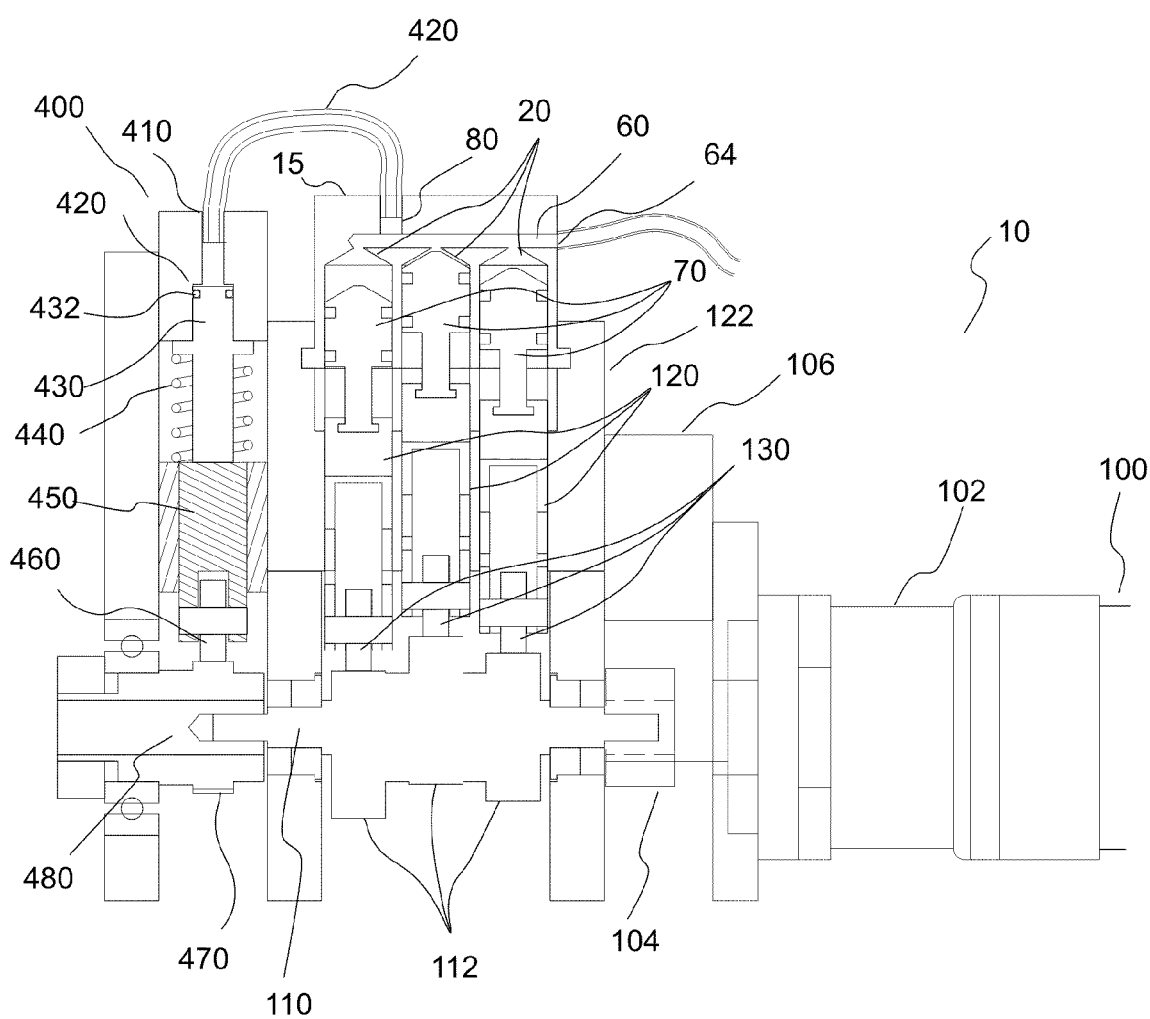
FIG. 4A illustrates a side, partially cross-sectional view of the pump system of FIG. 2A in connection with another embodiment of a compensating system or compensator.
Figure 4B:
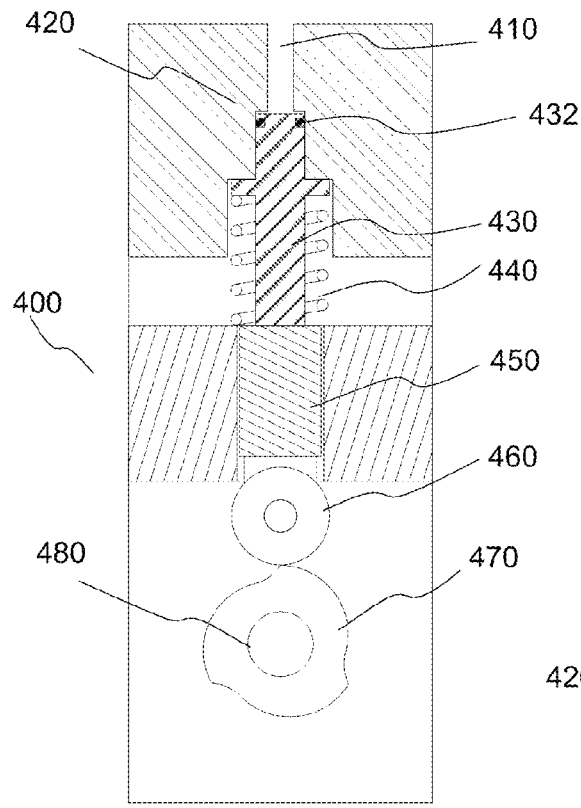
FIG. 4B illustrates a partially cross-sectional view of the compensating system of FIG. 4A wherein the fluid displacement member or piston thereof is in a forward position.
Figure 4C:
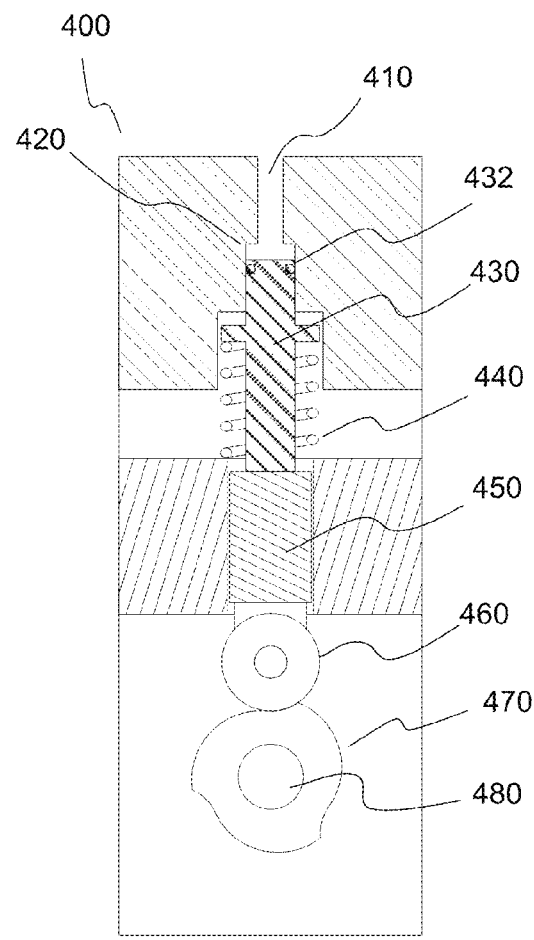
FIG. 4C illustrates a partially cross-sectional view of the compensating system of FIG. 4A wherein the fluid displacement member or piston thereof is in a rearward position.

FIGS. 4A through 4C illustrate another representative embodiment of a compensating system or compensator 400 in operative connection with pump system 10. System 400 can, for example, be placed in fluid connection with pressurized fluid in pump system 10 via port 80 in pressurizing unit 15 as described above in connection with compensating system 200. In the illustrated embodiment, an outlet 410 of system 400 is in fluid connection with port 80 via a conduit 420 (for example, tubing). Outlet 410 is in fluid connection with a chamber 420 of system 400. A fluid displacement member or piston 430 is slidably positioned within chamber 420. A sealing element such as an O-ring 432 forms a sealing engagement between piston 430 and an inner wall of chamber 420. Piston 430 is biased in position within chamber 420 by a biasing element such as a spring 440. The force exerted by spring 440 or another biasing element on piston 430 operates against the force exerted by the pressurized fluid to determine the position of piston 430 within chamber 420 and thereby a displacement volume. In that regard, the position of piston 430 within chamber 420 defines a stroke length of piston and corresponding volume of fluid within chamber 420 forward of piston 430 that can be expelled from system 400 into outlet conduit 60 upon advancement of piston 430.

Piston 430 is attached to or includes a piston extension or lifter 450, which is operatively connected to a cam follower 460 (for example, a bearing member connected to piston extension 450 via a pin). The down or rearward travel of piston 430 is limited by the spring load and by a multi-lobed cam element 470 on a cam shaft 480. In the illustrated embodiment, cam shaft 480 is coupled to or is formed as an extension of cam shaft 110. Cam element 470 and cam shaft 480 thus rotate at the same rate as cam shaft 110. As described further below, multi-lobed cam element 470 thereby operates to move piston 430 (changing the associated displacement volume) in synchronization with the operation of pistons 70.

At lower pressures, cam follower 460 will not contact cam element 470 at all points, resulting in a reduced stroke length of piston 430 and a corresponding smaller volume of fluid ejected from chamber 420 upon advancement of piston 430 as compared to higher fluid pressures at which cam follower 460 will contact cam element 470 over a wider range of rotation thereof. FIG. 4B illustrates piston 430 lifted by cam element 470. FIG. 4C illustrates piston 430 in a fully downward position and abutting cam element 470.

As illustrated in FIGS. 4B and 4C multi-lobed cam element 470 includes three radially outward extending lobes as there are three pistons 70 in pump system 10 and thus three regions of pressure drop associated with one revolution of cam shaft 110. Fewer or greater lobes (and/or more than one piston 430) can be provided on a cam element as required by a pressure or flow rate profile of an associated pump system. Cam element 470 is designed so that a compensating or displacement volume is ejected from system 400 during the downward spikes in pressure associated with pump system 420 as, for example, illustrated in FIG. 2D. As also illustrated in FIG. 2D, the area associated with the pressure drop spikes (and, thus, the associated drop in flow rate) increases as the average system fluid pressure increases. As described above, as the system pressure increases, the volume of fluid expelled from system 400 also increases. Thus, system 400 can more readily be designed to decrease pulsatility over an extended pressure range than can, for example, system 200.

Similar to compensating systems 200 and 300, system 400 decreases pressure/flow rate pulsatility by increasing and decreasing (that is, displacing) volume in the output volume or pressure side volume of pump unit 15. As described above, chamber 420 fills under pressure, and the fluid within chamber 420 is expelled by the rise in piston 430 resulting from the rotation of cam element 470. As described above, the rotation of tri-lobed cam element 470 is timed to pump system 10 so that pressure pulses of system 400 coincide with pressure drops associated with pump system 10.

As described above, FIG. 1H illustrates pressure as a function of time for pump system 10 operated at approximately 600 psi over one revolution. In a representative embodiment of system 400, a spring constant K was chosen to be 1080 lb/in. The force on piston 430 can be calculated by the equation $F=P \times A$, wherein P is fluid pressure and A is area. In several representative studies, Force=600 psi$\times$ 0.0925 in$^2$=55.6 lb. The spring compression is calculated by the formula F/K. 55.6 lb/1080 lb/in =0.0516 in compression. The Chamber volume V is equivalent to the compression distance multiplied by area A. In this representative embodiment, V=0.0925 in$^2 \times$0.0516 in.=0.0004778 in$^3$ (or 0.0785 ml). Expelling this volume from system 400 in an appropriately timed manner compensates for the pressure drops illustrated in FIG. 1H.

Figure 4D:
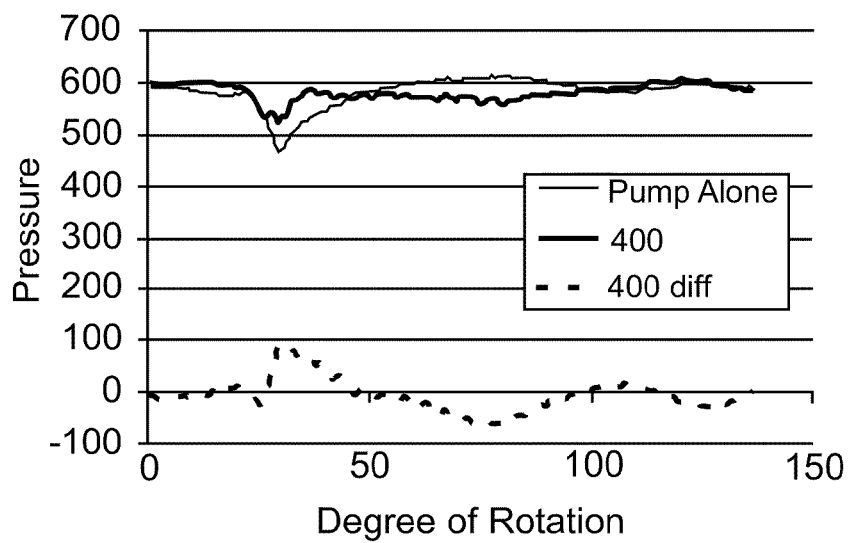
FIG. 4D illustrates pressure as a function of degree of rotation for one-third of a complete revolution)(120° of the cam shaft of the pump system of FIG. 1A for a system with and without the compensating system of FIG. 4A.

FIG. 4D illustrates a comparison of the resulting pressure wave form for a partial rotation (120 degrees) of cam shaft 110 for pump system 10 with and without compensating system 400. Further, the lower line in FIG. 4D sets forth the difference provided by compensating system 400 (that is, the change in system pressure provided by compensating system 400 as compared to operation without compensating system 400). At approximately 25 degrees of rotation, the relatively sharp rise in the lower line is associated with contact of one of the cam element lobes of cam element 470 with cam follower 460, causing a rise or advancement of piston 430 and expulsion of fluid from the volume of chamber 420 above or forward of piston 430. The relatively sharp rise corresponds to the sharp rise/increase in the cam lobe radius at this point. The drop in pressure after the peak corresponds to the drop/decrease of the cam lobe radius and the corresponding filling of the chamber volume forward of piston 430. Once spring 440 is compressed to a maximum amount as determined by fluid pressure at about 75 degrees, the pressure ceases dropping and returns to the baseline pressure.

In the embodiments studied, system 400 was not optimized to achieve optimal results. Further optimization can, for example, be achieved by adjustment of the timing of the start of the cam lobe lift, the rate of rise, the rate of drop (and the associated filling of the chamber volume forward of piston 430), the total volume of the piston, and the spring rate of spring 440, which controls/limits the fill volume forward of piston 430.

Figure 4E:
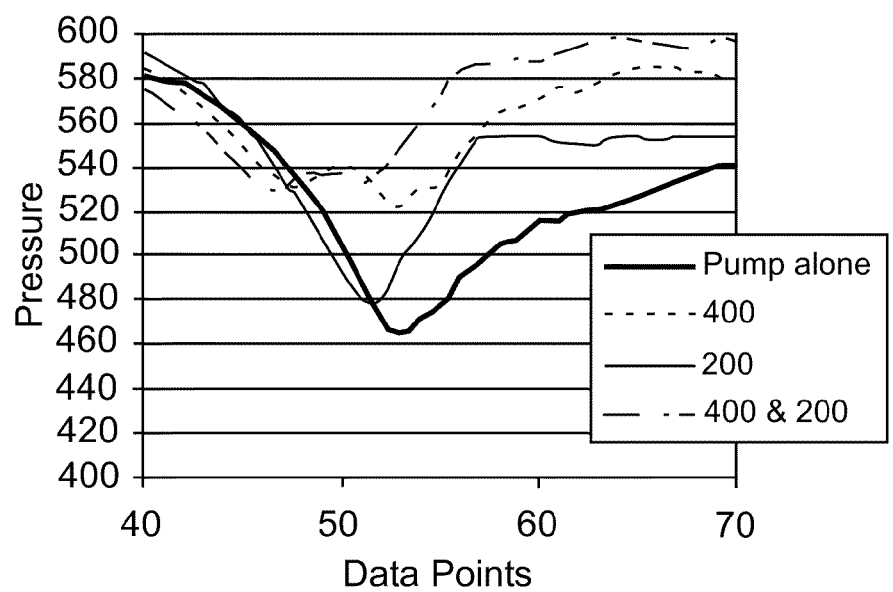
FIG. 4E illustrates pressure as a function of degree of rotation of the cam shaft of the pump system of FIG. 1A for a system without the compensating system of FIG. 4A (pump alone), with the compensating system of FIG. 4A (400), with the compensating system of FIG. 2A (200) and with both the compensating system of FIG. 2A and the compensating system of FIG. 4A (400 & 200).

FIG. 4E illustrates a magnified view of one of the low-pressure regions associated with pump system 10 and the effect of the addition of compensating system 200, compensating system 400 and both systems 200 and 400. As illustrated, multiple compensating systems as described herein (of the same or a different type or variety) can be placed in fluid connection with the pressurized fluid within system 10 to provide additive benefits/reduction in the degree of pulsatility.

FIGS. 5A through 5D illustrate another embodiment of a compensating system 600 that is similar in certain respects to compensating system 400. In that regard, system 600 includes an outlet 610 that can be placed in fluid connection with, for example, port 80 of pressurizing unit 15. Outlet 610 is in fluid connection with chamber 620 in which a fluid displacement member or piston 630 is slidably disposed. Piston 630 can, for example, form a sealing engagement with an inner wall of chamber 620 via one or more sealing elements such as O-ring 632. Piston 630 is in operative connection with a tri-lobe cam element 670 on a cam shaft 680 via a piston extension or lifter 650 and a cam follower 660 as described in connection with system 400.

In system 600, piston/volume displacement is adjustable via a displacement volume adjustment mechanism 690 rather than a pressure-balanced biasing mechanism, such as spring 440 in system 400. In the illustrated embodiment, adjustment element 690 includes an abutment member 694 to abut piston 630 or piston extension 650 to adjustably limit rearward movement of piston 630, thereby adjusting the volume of fluid forward of piston 430. In the illustrated embodiment, abutment member 694 includes a wedge-shaped abutment surface. Wedge-shaped abutment member 694 is adjustable in position (or moveable) to contact a sloped surface 654 of piston extension 650 to adjustably limit rearward travel of piston 630 within a range of settings. The range can, for example, extend from approximately zero or the innermost radius of cam element 670 (see FIG. 5A) to the lift/outermost radius of cam element 670 (see FIG. 5B).

Figure 5A:
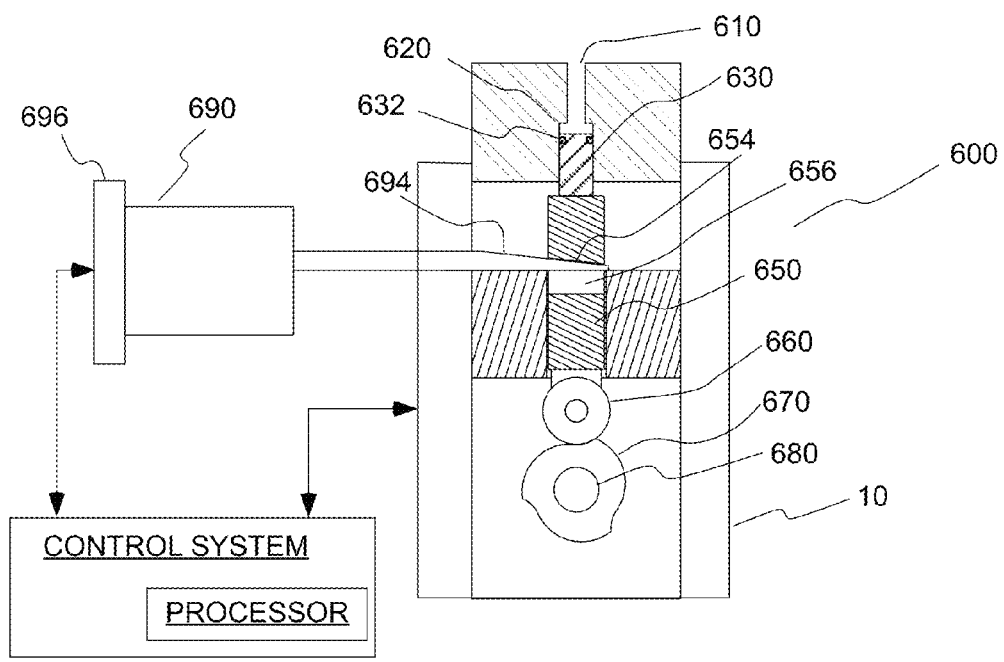
FIG. 5A illustrates a partially cross-sectional view of another embodiment of a compensating system or compensator wherein the fluid displacement member or piston thereof is in a forward position and a fluid displacement volume adjustment member for adjusting the volume of the fluid to be displaced is in a first position.
Figure 5B:
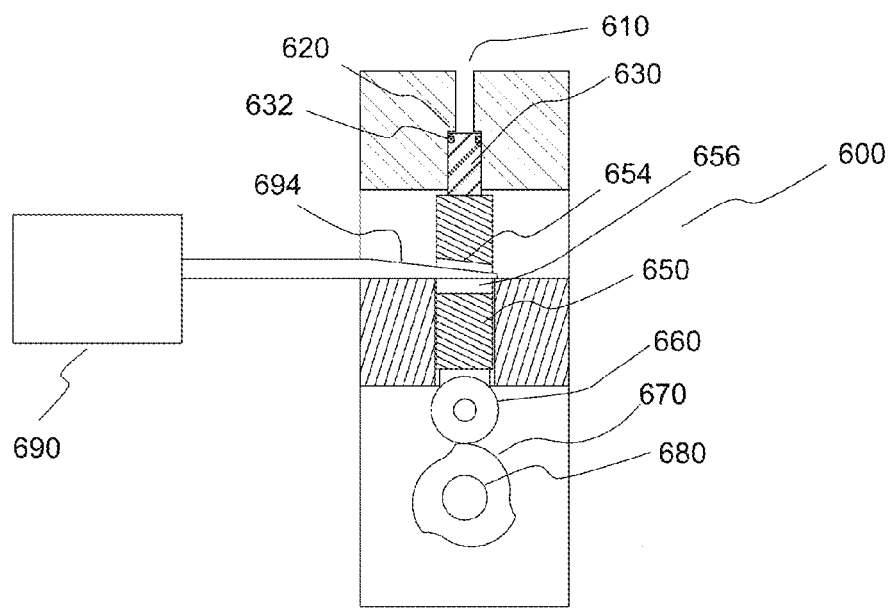
FIG. 5B illustrates a partially cross-sectional view of the compensating system of FIG. 5A wherein the fluid displacement member or piston thereof is in a rearward position.

The position of wedge-shaped abutment member 694 (and thus the fill volume of chamber 420) can, for example, be adjusted manually and/or by a control system for pump system 10 and associated compensating system 600 (see FIG. 5A). As known in the art, the control system can include one or more computer processors (for example, one or more microprocessors). Abutment member 694 can be set to one or more preset values determined, for example, by an experimentally and/or theoretically developed algorithm or look-up table. Alternatively, abutment member 694 can be set by an active servo system 696 that, for example, uses a pressure/pressure pulsatility measurement for feedback on the adjustment of abutment member 694.

Figure 5C:
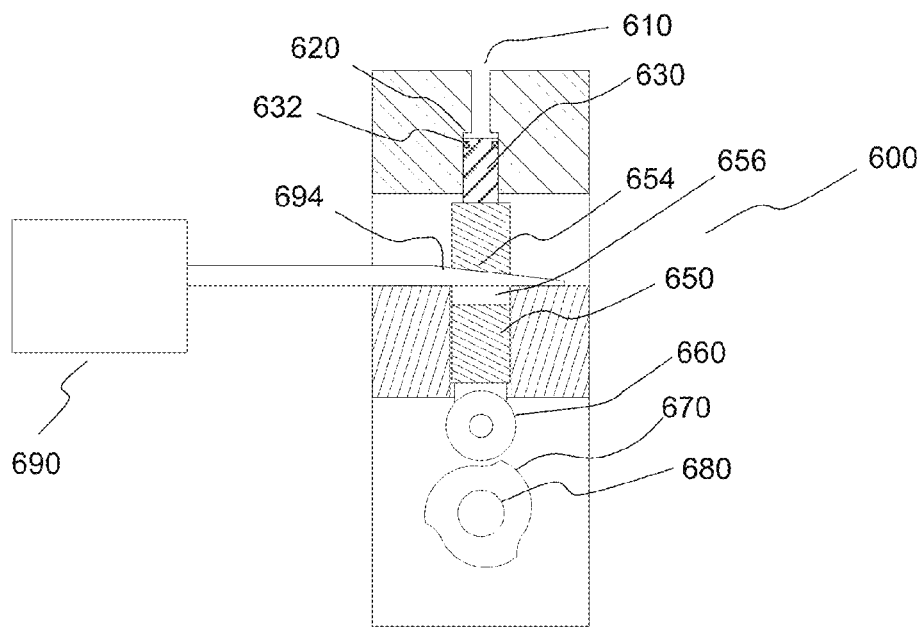
FIG. 5C illustrates a partially cross-sectional view of the compensating system of FIG. 5A wherein the fluid displacement member or piston thereof is in a forward position and the displacement volume adjustment member is in a second position.
Figure 5D:
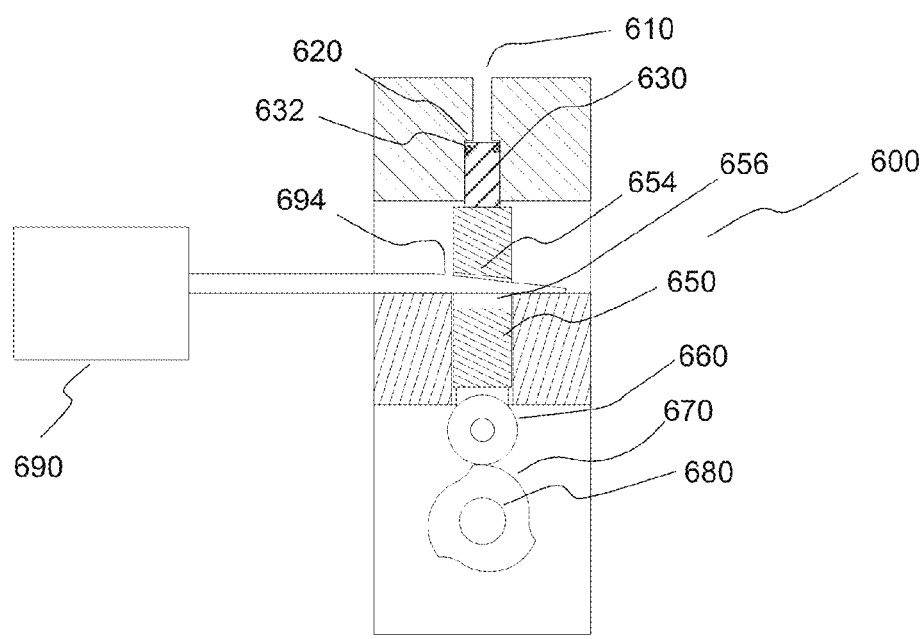
FIG. 5D illustrates a partially cross-sectional view of the compensating system of FIG. 5C wherein the fluid displacement member or piston thereof is in a rearward position.

FIG. 5A illustrates wedge-shaped abutment member 694 set/positioned for maximum fill volume within chamber 620. When cam element 670 rotates, it lifts/advances piston 630 (via cam follower 660 and extension or lifter 650), thereby expelling the fluid within the fill volume of chamber 620 (that is, the volume forward of piston 630 when piston 630 is in its rearwardmost position; see FIG. 5A). FIG. 5C illustrates wedge-shaped abutment member 694 set/positioned to the right (in the orientation of FIGS. 5A through 5C) of its position in FIGS. 5A and 5B such that it is contacted by piston extension surface 654 at a "higher" position on wedge shaped abutment member 654, thereby reducing the rearward travel of piston 630 and the associated fill volume. FIG. 5D illustrates rotation of cam element 670 such that one of the cam lobes contacts cam follower 660 at the maximum lift position in expelling the fill volume of fluid from chamber 620.

In the embodiment illustrated in FIGS. 5A through 5D, piston extension 650 includes a passage 656 therethrough, through which wedge-shaped abutment member 694 is moved or slid to adjust or set the abutment position/fill volume.

Figure 6A:
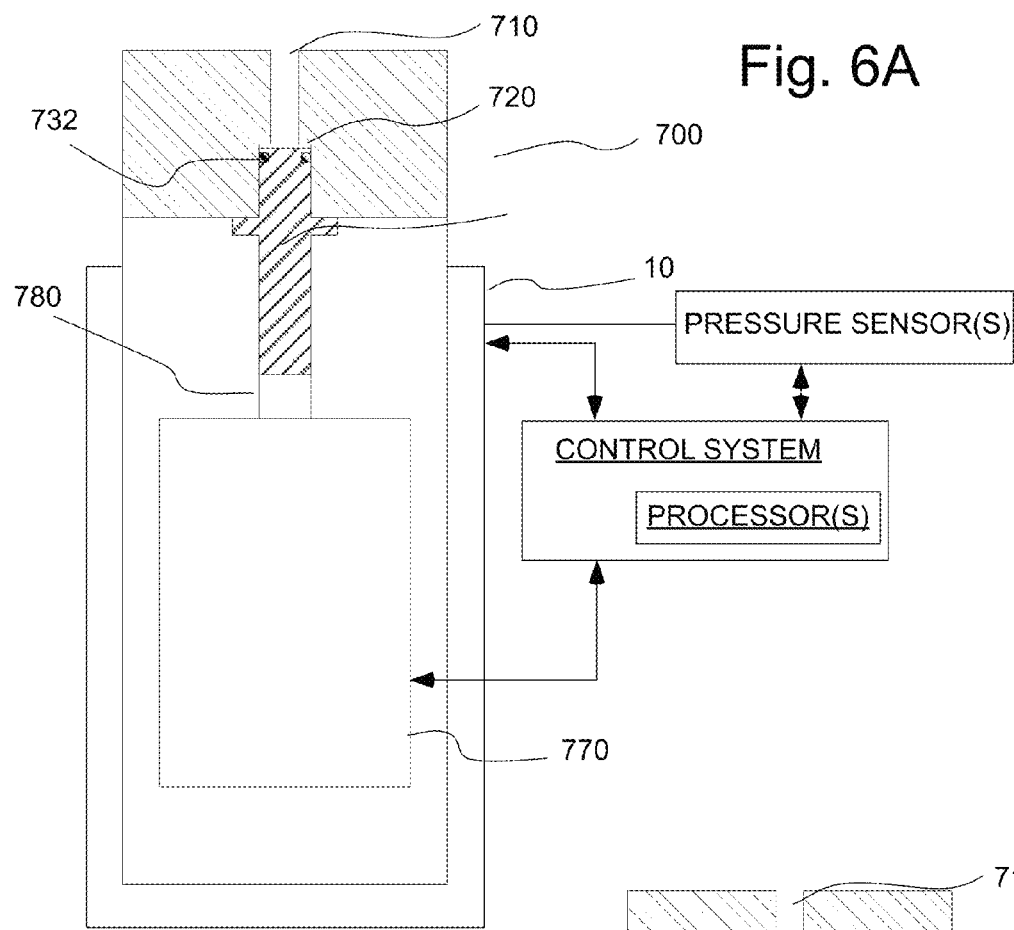
FIG. 6A illustrates a partially cross-sectional view of another embodiment of a compensating system or compensator wherein the fluid displacement member or piston thereof is in a forward position and a fluid displacement adjustment member is in a first position.
Figure 6B:
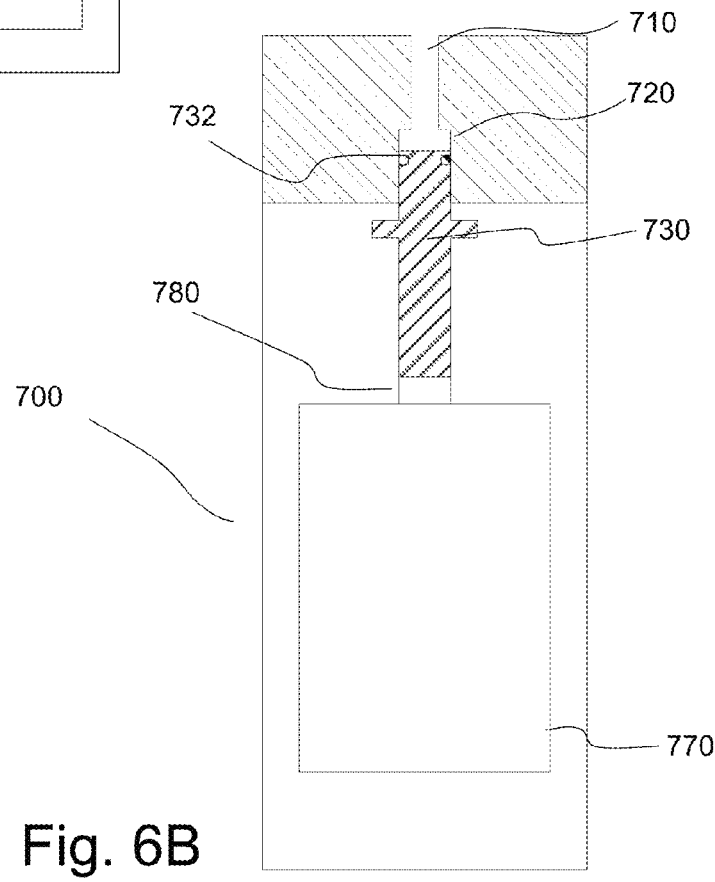
FIG. 6B illustrates a partially cross-sectional view of the compensating system of FIG. 6A wherein the fluid displacement member or piston thereof is in a rearward position.

FIGS. 6A and 6B illustrate another embodiment of a compensating system or compensator 700 that includes an outlet 710 that can be placed in fluid connection with, for example, port 80 of pressurizing unit 15. Outlet 710 is in fluid connection with chamber 720 in which fluid displacement member or piston 730 is slidably disposed. Piston 730 can, for example, form a sealing engagement with an inner wall of chamber 720 via one or more sealing elements such as O-ring 732 as described above. In the embodiment of FIGS. 6A and 6B, piston 730 is in operative connection with a powered drive, a controlled drive system or a linear actuator system 770 which is in operative connection with a drive member 780. A number of drive systems or actuator systems 770 are suitable for use with piston 730. Suitable drive systems include, for example, speaker motors, linear motors, pneumatic cylinders, piezoelectric actuators, or a motor with a linear drive such as a ball screw. In general, drive system 770 provides for movement of piston 730, which can be used to provide a volume displacement or pressure variation/pulse to counteract the pressure fluctuations arising, for example, from pulsatility of pump system 10 (or other pump systems) to minimize pressure/flow rate variances. Drive system 770 can, for example, be used to operate/control any type of linear drive or actuator.

Drive or actuator system 770 is operated to move piston 730 in a controlled/timed manner to compensate for decreases and/or increases in pressure of pump system 10. Internal fluid pressure (or flow rate) can, for example, be measured and a computer processor of a control system can be used to operate drive system 770 to minimize pulsatility at least in part on the basis of the measured pressure (or flow rate). Additionally or alternatively, drive system 770 can be programmed using an algorithm based, for example, on speed and/or pressure to set a required response of piston 730 to minimize pulsatility.

As described above, piston 730 is moved to displace/fill a determined fill volume of chamber 720 when fluid pressure in the system is high, thereby reducing peak pressure. As the fluid pressure decreases, piston 730 is moved forward, thereby displacing/expelling fluid and increasing pressure in the system. The actuation/movement of piston 730 thereby reduces overall changes in pressure (from a determined or desired pressure profile) in the system.

Figure 7A:
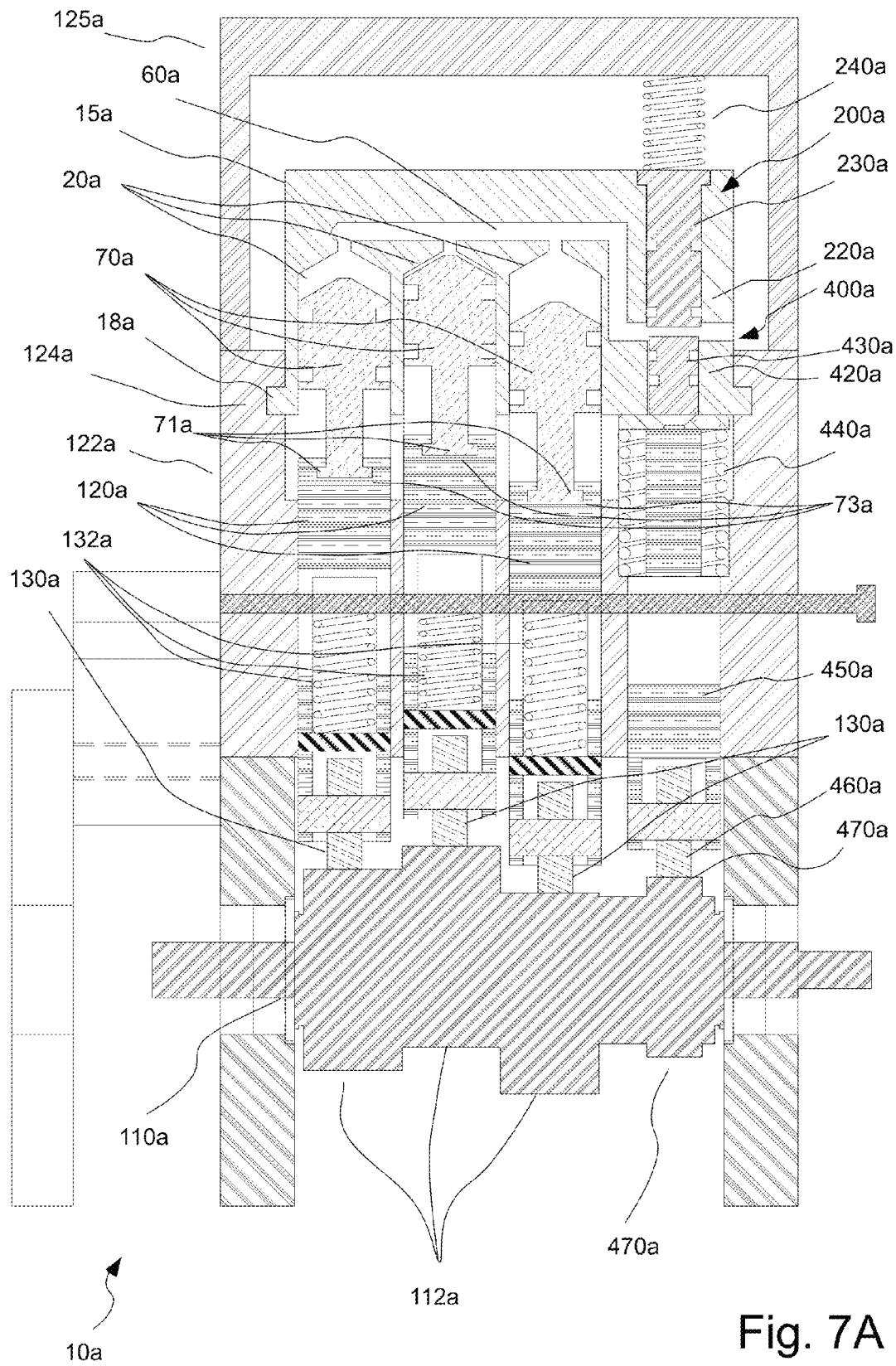
FIG. 7A illustrates a side, cross-sectional view of another embodiment of a pump system including two compensating systems, wherein a removable pressurizing unit including the compensating systems is in operative connection with the drive system of the pump system.
Figure 7B:
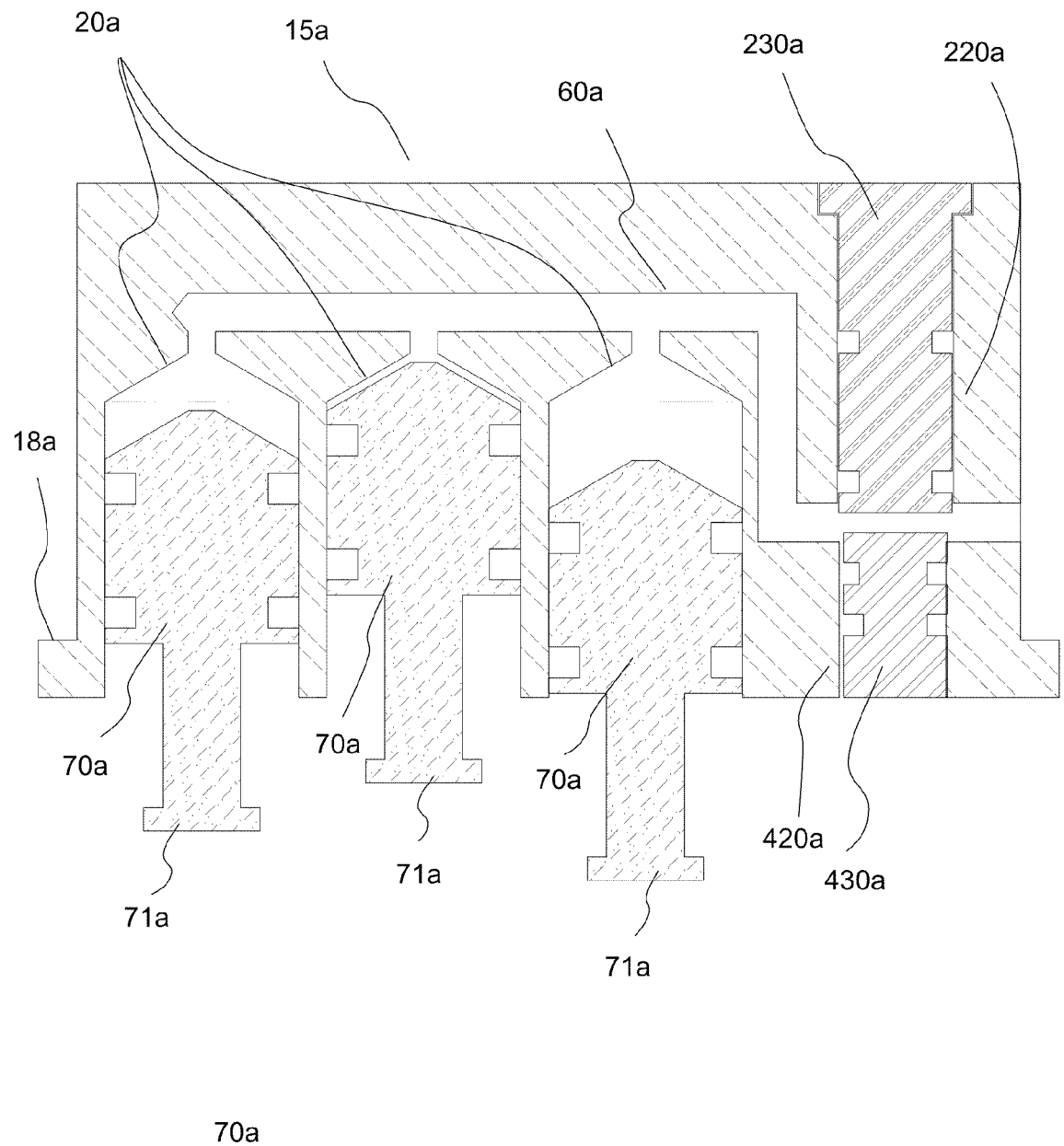
FIG. 7B illustrates a side, cross-sectional view of the pressurizing unit which is removed from connection with the drive system
Figure 7C:
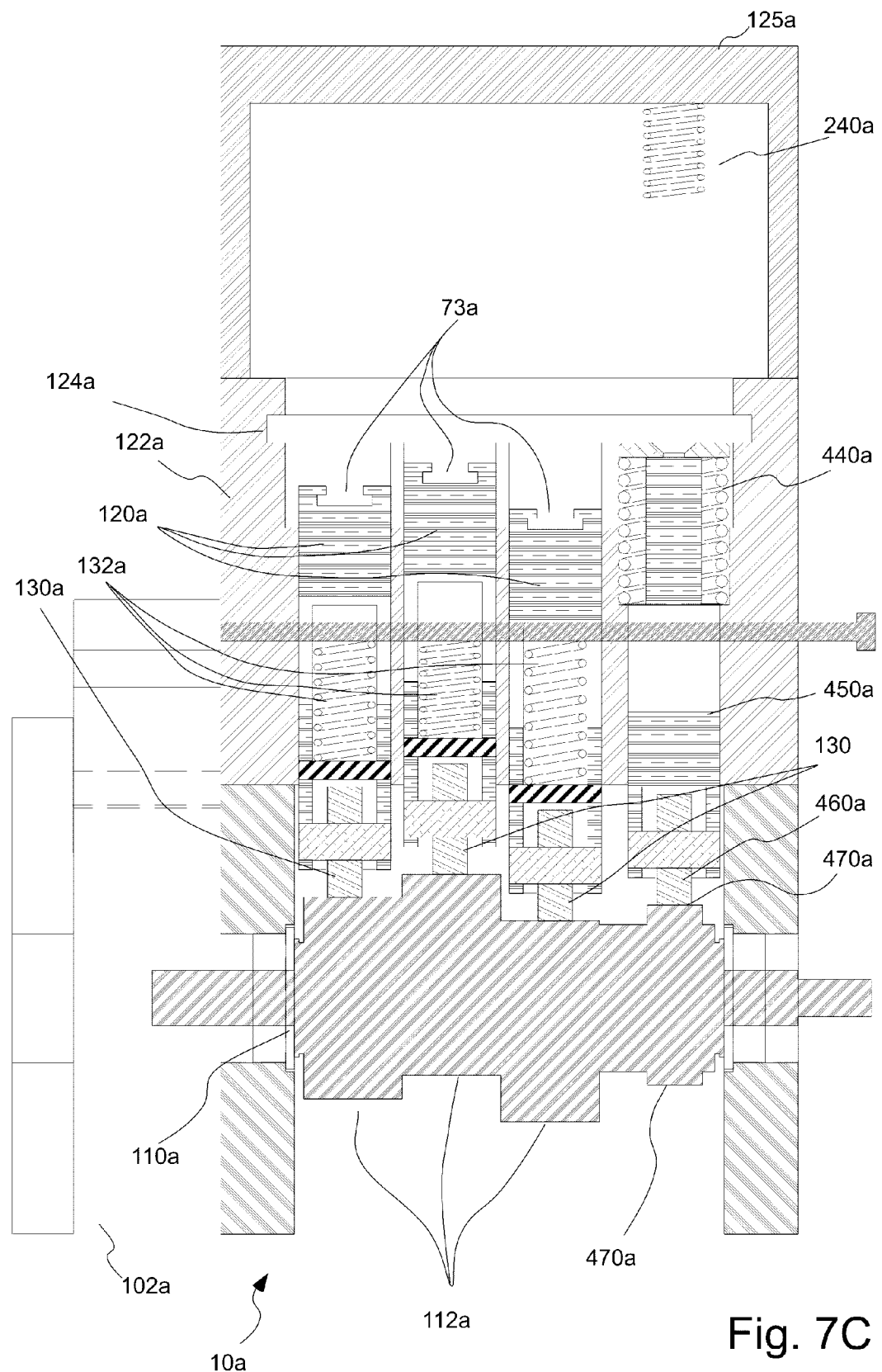
FIG. 7C illustrates a side, cross-sectional view of the drive system of the pump system with the pressurizing unit removed from connection therewith.

FIGS. 7A through 7C illustrate an embodiment of a pump system 10a similar in operation to pump system 10. A drive mechanism such as drive mechanism 100 (not shown in FIGS. 7A through 7C) is in operative connection with a timing mechanism or system such as a cam shaft 110a. Cam shaft 110a includes three cam lobes 112a along the length thereof to drive pistons 70a of a pressurizing unit 15a in a timed sequence. Cam lobes 112a of cam shaft 110 are in operative connection with cam lifters or piston extension members 120a which are reciprocally moveable through a lifter block 122a and terminate on one end thereof in attachment members which releasably cooperate with corresponding attachment members on pistons 70a as described above. Piston extension members 120a are placed in operative connection with cam shaft lobes 112a via cam lifters 130a, which are in operative connection with lifter springs 132a as described above.

Pressurizing unit 15a can, for example, be placed in operative connection with lifter block 122a via a flange 18a, which can be seated in a seating 124a of lifter block 122a. The fluid contacting portions of system 10a, including pressurizing unit 15a (including pistons 70a thereof) can be readily removed from connection with drive mechanism 100.

Pressurizing unit 15a can be disposable (for example, on a per-patient, per time or other basis) to, for example, reduce or eliminate the risk of cross-patient contamination. FIG. 7B illustrates pressurizing unit 15a removed from connection from the remainder of pump system 10a.

In the embodiment of FIGS. 7A through 7C, removable pressurizing unit 15a includes the fluid displacement/contacting components of a first compensating system 200a (which is similar in operation to compensating system 200) and a second compensating system 400a (which is similar in operation to compensating system 400). Compensating system 200a includes a chamber or cylinder 220a formed in pressurizing unit 15a. A fluid displacement member or piston 230a is slidably positioned within chamber 220a. Similarly, compensating system 400a includes a chamber or cylinder 420a formed in pressurizing unit 15a. A fluid displacement member or piston 430a is slidably positioned within chamber 420a. In the illustrated embodiment, each of piston 230a and piston 430a can, for example, be moved to extend into the volume of outlet channel 60a or to be withdrawn into chambers 220a and 420a, respectively (and in the manner described in connection with compensating system 200 and compensating system 400), to change the pressurized volume within pump unit 15a and thereby reduce pulsatility in pressure/flow rate.

In the embodiment of FIGS. 7A through 7C, piston 430a is attached to or includes a piston extension or lifter 450a, which is movable through lifter block 122a and is operatively connected to a cam follower 460a. The downward or rearward travel (and associated displacement volume) of piston 430a can, for example, be limited/adjusted (as, for example, described in connection with compensating system 400) by a spring 440a and contact with multi-lobed cam element 470a. As also described in connection with compensating system 400, cam follower 460a is contacted by multi-lobed cam element 470a to provide timed actuation/movement of piston 430a. In the illustrated embodiment, multi-lobed cam element 470a is attached to or formed on cam shaft 110a. Cam element 470a thus rotates at the rotation rate of cam shaft 110a. Multi-lobed cam element 470a thereby operates to move piston 430a (changing the associated displacement volume) in synchronization with the operation of pistons 70a.

Pump system 10a further includes a frame member 125a to which a biasing spring 240a is connected to bias piston 230a against the force exerted thereon by the pressurized fluid as described in connection with spring 240 of compensating system 200.

FIG. 7C illustrates pump system 10a with pressurizing unit 15a removed from connection therewith. To connect pressurizing unit 15a to the remainder of pump system 10a, flange 18a is slid into seating 124a, while flanges 71a on pistons 70a are slid into cooperating slots 73a formed on the upper ends of piston extension members 120a. After use of pressurizing unit 15a to pressurize fluid (for example, in connection with a single patient), pressurizing unit can be removed from connection with the remainder of pump system 10a for disposal. Another pressurizing unit 15a can then be placed in operative connection with the remainder of pump system 10a.

As described above, pressurizing unit 15a (as well as pressurizing unit 15) can, for example, be fabricated from polymeric materials, metals, ceramic and/or other materials. Pistons 70a, 230a and 430a can be fabricated from similar materials. Suitable materials can readily be identified by those skilled in the art for a particular range of flow rates and pressures using accepted engineering principles.

In several of the embodiments of the compensating systems described above, the compensating system is placed in fluid connection with the pressurized side of the pump (for example, in fluid connection with common outlet 60 or 60a of pressurizing unit 15 or 15a, respectively). The compensating systems hereof can, however, be placed in connection with a volume of the pressurized fluid at any point between the pump system and the patient. Typically, the compensating system can be placed in fluid connection with the pressurized fluid at any point between the pump system and a catheter. Compensating system 300 can, for example, be placed in-line with a fluid conduit (for example, tubing) in connection between pressurizing unit 15 or 15a and the catheter. Compensating systems 200, 400, 600 and 700 can, for example, be placed in fluid connection with such a fluid conduit by, for example, a T-connector. Compensating systems 300 can also, for example, be closed on one end thereof and placed in fluid connection with such a fluid conduit by, for example, a T-connector.

Furthermore, the operation of the compensating systems described herein had been discussed in connection with reducing or minimizing pressure variations or pulsatility in which a pump system is operated at a generally constant average pressure or flow rate. The compensating systems can also be used to reduce transient pressure variations or pulsatility in a flow scheme in which pressure/flow are being changed (for example, increased or decreased in a linear or other manner).

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for delivery of a medical fluid to a patient comprising:

a pump system comprising a pressurizing unit to pressurize the medical fluid and a drive system in operative connection with the pressurizing unit, the pump system exhibiting a variation in pressure during operation; and a compensating system in fluid connection with the medical fluid pressurized by the pressurizing unit, the compensating system defining a chamber having a displacement volume in fluid connection with the pressurized medical fluid wherein the displacement volume is altered to alter the variation in pressure, the compensating system comprising a piston that is reciprocally moveable within the chamber to alter the displacement volume of the chamber, a first end of the piston of the compensating system being in operative connection with a drive mechanism adapted to actively move the piston of the compensating system in a manner dependent upon timing of actuation of the pressurizing unit, a second end of the piston of the compensating system being biased against the force of the pressurized medical fluid by a compressible biasing mechanism having a predetermined compressibility, wherein the piston of the compensating system is actively moved by the drive mechanism against the biasing force of the compressible biasing mechanism to reduce pulsatility of the pressurized medical fluid over a range of fluid pressure within the operating pressure range of the pump system.

2. The system of claim 1, wherein the pressurizing unit comprises a plurality of actuatable pressurizing members and the compensating system reduces pulsatility of the pressurized medical fluid during flow resulting from timed actuation of the plurality of pressurizing members.

3. The system of claim 2, wherein the plurality of actuatable pressurizing members comprise a plurality of pistons.

4. The system of claim 1, wherein the compressible biasing mechanism is a spring.

5. The system of claim 3, wherein the plurality of actuatable pressurizing members are actuated in a timed manner by the drive system, and wherein the drive mechanism moves the piston of the compensating system in a manner dependent upon a timing of actuation of the plurality of actuatable pressurizing members.

6. The system of claim 5, wherein the drive system comprises a multi-lobed cam element that is rotated to time movement of each of the plurality of actuatable pressurizing members.

7. The system of claim 6, wherein a number of lobes of the multi-lobed cam element is determined by a number of the plurality of actuatable pressurizing members.

8. The system of claim 7, wherein the pump system comprises a rotatable timing shaft to actuate the plurality of actuatable pressurizing members in the timed manner and wherein the multi-lobed cam element is coupled to the rotatable timing shaft.

9. The system of claim 8, wherein the piston of the compensating system is slidably positioned within a chamber and forms a sealing engagement with an inner wall of the chamber.

10. The system of claim 9, wherein a rearwardmost position of the piston of the compensating system is adjustable within the chamber to adjust an extent to which the piston can alter the displacement volume.

11. The system of claim 10, wherein the compressible biasing mechanism is a spring.

12. The system of claim 10, further comprising an abutment element to abut the piston of the compensating system and to adjust the rearwardmost position of the piston.

13. The system of claim 1, wherein the compensating system further comprises a second piston slidably positioned within a second chamber and forming a sealing engagement with an inner wall of the second chamber, and an actuator system to control position of the second piston within the second chamber, the actuator system being in communicative connection with a control system.

14. The system of claim 1, wherein the compensating system is in fluid connection with an outlet channel within the pressurizing unit.

15. The system of claim 1, wherein the pressurizing unit is removable from connection with the drive system.

* * * * *